US006328688B1

(12) United States Patent
Borst et al.

(10) Patent No.: US 6,328,688 B1
(45) Date of Patent: *Dec. 11, 2001

(54) METHOD AND APPARATUS FOR TEMPORARILY IMMOBILIZING A LOCAL AREA OF TISSUE

(75) Inventors: Cornelius Borst; Hendricus J. Mansvelt Beck, both of Bilthoven; Paul F. Gründeman, Amsterdam; Erik W. L. Jansen, Zeist, all of (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/493,568

(22) Filed: Jan. 28, 2000

Related U.S. Application Data

(60) Division of application No. 09/334,531, filed on Jun. 19, 1999, which is a division of application No. 08/725,371, filed on Oct. 3, 1996, now Pat. No. 6,015,378, which is a continuation-in-part of application No. 08/531,363, filed on Sep. 20, 1995, now Pat. No. 5,836,311.

(51) Int. Cl.[7] ........................................................ A61F 2/00
(52) U.S. Cl. ............................ 600/37; 606/201; 128/897
(58) Field of Search ................................ 600/37, 201–2; 128/897–8

(56) References Cited

U.S. PATENT DOCUMENTS

| | | |
|---|---|---|
| 452,131 | 5/1891 | Haughawout . |
| 3,577,982 | 5/1971 | La Par .................... 128/2 R |
| 3,720,433 | 3/1973 | Rosfelder . |
| 3,783,873 | 1/1974 | Jacobs .................. 128/303 R |
| 3,786,815 | 1/1974 | Ericson ................... 128/321 |

(List continued on next page.)

FOREIGN PATENT DOCUMENTS

| | | |
|---|---|---|
| 0293760 A2 | 5/1987 | (DE) . |
| 9004513 | 4/1990 | (DE) . |
| 29708050 | 5/1997 | (DE) . |

(List continued on next page.)

OTHER PUBLICATIONS

Th. LOavergne et al. PACE, vol. 12 Jan. 1989, Part II pp. 177–186) "Transcatheter Radiofrequency Ablation of Atrial Tissue Using a Suction Catheter".

(List continued on next page.)

*Primary Examiner*—Robert L. Nasser
(74) *Attorney, Agent, or Firm*—Thomas G. Berry; Michael J. Jaro; Stephen W. Bauer

(57) ABSTRACT

A method and apparatus for temporarily immobilizing a local area of tissue. In particular, the present invention provides a method and apparatus for temporarily immobilizing a local area of heart tissue to thereby permit surgery on a coronary vessel in that area without significant deterioration of the pumping function of the beating heart. The local area of heart tissue is immobilized to a degree sufficient to permit minimally invasive or micro-surgery on that area of the heart. The present invention features a suction device to accomplish the immobilization. The suction device is coupled to a source of negative pressure. The suction device has a series of suction ports on one surface. Suction through the device causes suction to be maintained at the ports. The device further is shaped to conform to the surface of the heart. Thus, when the device is placed on the surface of the heart and suction is created, the suction through the ports engages the surface of the heart. The suction device is further fixed or immobilized to a stationary object, such as an operating table or a sternal or rib retractor. Thus, the local area of the heart near the suction device is temporarily fixed or immobilized relative to the stationary object while suction is maintained. In such a fashion, the coronary artery may be immobilized even though the heart itself is still beating so that a bypass graft may be performed. In addition the suction device may be used in either a conventional, open-chest environment or in a minimally-invasive environment, e.g. endoscopic.

64 Claims, 21 Drawing Sheets

U.S. PATENT DOCUMENTS

| | | |
|---|---|---|
| 3,858,926 | 1/1975 | Ottenhues . |
| 3,916,909 | 11/1975 | Kletschka et al. ............... 128/354 |
| 3,951,138 | 4/1976 | Akopov ............................. 128/17 |
| 3,983,863 | 10/1976 | Janke et al. ...................... 128/1 R |
| 3,999,795 | 12/1976 | Barker ............................ 294/64 R |
| 4,047,532 | 9/1977 | Phillips et al. . |
| 4,049,002 | 9/1977 | Kletschka et al. ............... 128/318 |
| 4,096,864 | 6/1978 | Kletschka et al. ............... 128/354 |
| 4,306,561 | 12/1981 | De Medinaceli ............ 128/303.13 |
| 4,314,568 | 2/1982 | Loving ............................. 128/327 |
| 4,350,160 | 9/1982 | Kolesov ........................ 128/334 R |
| 4,366,819 | 1/1983 | Kaster . |
| 4,368,736 | 1/1983 | Kaster . |
| 4,447,227 | 5/1984 | Kotsanis ............................ 604/95 |
| 4,463,980 | 8/1984 | Orii ................................ 294/64 R |
| 4,627,421 | 12/1986 | Symbas et al. . |
| 4,637,377 | 1/1987 | Loop . |
| 4,646,747 | 3/1987 | Lundback . |
| 4,688,570 | 8/1987 | Kramer et al. .................... 128/305 |
| 4,711,247 | 12/1987 | Fishman .......................... 128/743 |
| 4,718,418 | 1/1988 | L'Esperence, Jr. . |
| 4,726,356 | 2/1988 | Santilli et al. .................... 128/20 |
| 4,736,749 | 4/1988 | Ludback . |
| 4,767,142 | 8/1988 | Takahashi et al. .............. 294/64.1 |
| 4,808,163 | 2/1989 | Laub . |
| 4,854,318 | 8/1989 | Solem et al. . |
| 4,865,019 | 9/1989 | Phillips . |
| 4,892,343 | 1/1990 | Hall ................................ 294/64.1 |
| 4,904,012 | 2/1990 | Nishiguchi et al. ............... 294/64 |
| 4,925,443 | 5/1990 | Heilman et al. .................. 600/16 |
| 4,955,896 | 9/1990 | Freeman .......................... 606/210 |
| 4,962,758 | 10/1990 | Lasner et al. . |
| 4,973,300 | 11/1990 | Wright ............................. 600/37 |
| 4,989,587 | 2/1991 | Farley . |
| 4,991,578 | 2/1991 | Cohen . |
| 5,009,660 | 4/1991 | Clapham . |
| 5,011,469 | 4/1991 | Buckberg et al. . |
| 5,053,041 | 10/1991 | Ansari et al. . |
| 5,098,369 | 3/1992 | Heilman et al. .................. 600/16 |
| 5,108,412 | 4/1992 | Krumeich et al. . |
| 5,119,804 | 6/1992 | Anstadt ............................. 12/64 |
| 5,131,905 | 7/1992 | Grooters ........................... 600/16 |
| 5,133,737 | 7/1992 | Grismer ........................... 606/205 |
| 5,167,223 | 12/1992 | Koros et al. . |
| 5,171,254 | 12/1992 | Sher . |
| 5,207,467 | 5/1993 | Smith ............................ 294/64.1 |
| 5,287,861 | 2/1994 | Wilk . |
| 5,290,082 | 3/1994 | Palmer et al. .................. 294/64.1 |
| 5,300,087 | 4/1994 | Knoepfler ........................ 606/207 |
| 5,324,087 | 6/1994 | Shimose et al. ................ 294/64.1 |
| 5,336,252 | 8/1994 | Cohen ............................. 607/119 |
| 5,365,921 | 11/1994 | Bookwalter et al. . |
| 5,372,124 | 12/1994 | Takayama et al. ................. 128/4 |
| 5,374,277 | 12/1994 | Hassler . |
| 5,383,840 | 1/1995 | Heilman et al. .................. 600/17 |
| 5,417,709 | 5/1995 | Slater ............................. 606/205 |
| 5,425,705 | 6/1995 | Evard et al. . |
| 5,437,651 | 8/1995 | Todd et al. . |
| 5,452,733 | 9/1995 | Sternman et al. ............... 128/898 |
| 5,472,438 | 12/1995 | Schmit et al. . |
| 5,509,890 | 4/1996 | Kazama ............................ 600/37 |
| 5,545,123 | 8/1996 | Ortiz et al. . |
| 5,556,147 | 9/1996 | Somekh et al. ................ 294/64.1 |
| 5,607,421 | 3/1997 | Jeevanandam et al. ............ 606/15 |
| 5,613,937 | 3/1997 | Garrison et al. ................. 600/201 |
| 5,667,624 | 9/1997 | Akimoto et al. ................. 156/389 |
| 5,702,420 | 12/1997 | Sterling et al. .................. 606/205 |
| 5,727,569 | 3/1998 | Benetti et al. ................... 128/898 |
| 5,749,892 | 5/1998 | Vierra et al. ..................... 600/204 |
| 5,782,746 * | 7/1998 | Wright ............................. 600/37 |
| 5,799,661 | 9/1998 | Boyd et al. ...................... 128/898 |
| 5,807,243 | 9/1998 | Vierra et al. ..................... 600/204 |
| 5,827,216 | 10/1998 | Igo et al. .......................... 604/21 |
| 5,836,311 * | 11/1998 | Borst et al. ........................ 600/37 |
| 5,875,782 | 3/1999 | Ferrari et al. ................... 128/898 |
| 5,894,843 | 4/1999 | Benetti et al. ................... 128/898 |
| 5,906,607 | 5/1999 | Taylor et al. ........................ 606/1 |
| 5,927,284 * | 7/1999 | Borst et al. ........................ 600/37 |
| 6,015,378 | 1/2000 | Borst et al. ........................ 600/37 |
| 6,019,722 * | 2/2000 | Spence et al. ..................... 600/37 |
| 6,032,672 | 3/2000 | Taylor ............................ 128/898 |
| 6,063,021 * | 5/2000 | Hossain et al. .................... 600/37 |
| 6,071,235 | 6/2000 | Furnish et al. .................. 600/235 |
| 6,110,187 | 8/2000 | Donlon ............................ 606/151 |
| 6,139,492 | 10/2000 | Vierra et al. ..................... 600/204 |

FOREIGN PATENT DOCUMENTS

| | | |
|---|---|---|
| 0 167 345 A1 | 1/1986 | (EP) . |
| 0 293 760 A3 | 5/1988 | (EP) . |
| 0 432 560 A2 | 11/1990 | (EP) . |
| 0 630 629 A1 | 12/1994 | (EP) . |
| 0 668 058 A1 | 8/1995 | (EP) . |
| 0 808 606 A1 | 11/1997 | (EP) . |
| 0 920 835 A1 | 6/1999 | (EP) . |
| 2 140 695A | 12/1984 | (GB) . |
| 2 214 428A | 9/1989 | (GB) . |
| 2 214 428B | 6/1991 | (GB) . |
| 2267827 | 12/1993 | (GB) . |
| WO 87/04081 | 7/1987 | (WO) . |
| WO 88/00481 | 1/1988 | (WO) . |
| WO 94/03142 | 2/1994 | (WO) ........................ A61H/31/00 |
| WO 94/14383 | 7/1994 | (WO) . |
| WO 94/14715 | 7/1994 | (WO) . |
| 9418881 | 9/1994 | (WO) . |
| WO 94/18881 | 9/1994 | (WO) . |
| 9501757 | 1/1995 | (WO) . |
| WO 95/01757 | 1/1995 | (WO) . |
| 9514715 | 6/1995 | (WO) . |
| 9515715 | 6/1995 | (WO) . |
| WO 95/15715 | 6/1995 | (WO) . |
| WO 95/17127 | 6/1995 | (WO) . |
| 9600033 | 1/1996 | (WO) . |
| WO 96/00033 | 1/1996 | (WO) . |
| WO 97/10753 | 3/1997 | (WO) . |
| WO 98/10705 | 3/1998 | (WO) . |
| WO 98/17182 | 4/1998 | (WO) . |
| WO 98/27869 | 7/1998 | (WO) . |
| WO 99/16367 | 4/1999 | (WO) . |

OTHER PUBLICATIONS

Jrnl of Society of Thoracic Surgeons and the Southern Thoracic Surgical Assn. vol. 19 No. 1 Jan. 1975–Trapp et al. Placement of coronary Artery Bypass Graft Without Pump Oxygenator.

Society of Thoracic Surgeons 1993. Fanning et al, Reoperative Coronary Artery Bypass Grafting Without Cardiopulmonary Bypass:

Abstract: "Closed Chest Coronary Artery Bypass with Cardiopletic Arrest in the Dog", Stevens et al 67th Scientific Sessions.

Mammary Artery–Coronary Artery Anastomosis as Method of Treatment for Angina Pectoris, V.I Kolessov, MD/Thoracic and Cardiovascular Surgery, vol. 54, No. 4, October 1967 pp. 535–544.

Direct Myocardial Revascularization by Saphenous Vein Graft, R.G. Favaloro, MD; DG Effler, MD; LK Groves, MD; WG Sheldon, MD; and FM Sones, Jr., MD/ The Annals of Thoracic Surgery, vol. 10, No. 2, August 1970.

A Simple Technique and Device to Provide a Bloodless Operative Field in Coronary Artery Surgery Without Cross-Clamping the Aorta, M. Riahi, RJ Schlosser and LA Tomastis/The Journal of Thoracic and Cardiovascular Surgery, vol. 66, No. 65, December 1973, pp. 974–978.

To Use or Not To Use the Pump Oxygenator in Coronary Bypass Operatio–ns, Drs. WG Trapp and R. Bisarya/The Annals of Thoracic Surgery, vol. 19, No. 1, January 1975, pp. 108–109.

A Prospective Evaluation of the Pulsatile Assist Device, GL Zumbro, Jr., MD; G Shearer, CCP; ME Fishback, MD; and RF Galloway, MD/ The Annals of Thoracic Surgery, vol. 28, No. 2, August 1979, pp. 269–273.

Preservation of Interventricular Septal Function in Patients Having Coronary Artery Bypass Grafts Without Cardiopulmonary Bypass, CW Akins, MD; CA Boucher, MD; and GM Pohost, MD/ American Heart Journal, vol. 107, No. 2, February 1984, pp. 304–309.

Coronary Artery Revascularization Without Cardiopulmonary Bypass, R. Archer, DO; DA Ott, MD; R. Parravicini, MD; DA Cooley, MD; GJ Reul, MD; OH Frazier, MD; JM Duncan, MD; JJ Livesay, MD and WE Walker, MD, Texas Heart Institute Journal, vol. 11, No. 1, March 1984, pp. 52–57.

Direct Myocardial Revascularization Without Cardiopulmonary Bypass, E. Buffolo; JCS Andrade, J Succi; LEV Leao; and C Gallucci. Thoac. Cardiovasc. Surgeon, 33 (1985) pp. 26–29.

Direct Coronary Surgery with Saphenous Vein Bypass Without Eigher Cardiopulmonary Bypass or Cardiac Arrest, FJ Benetti, The Journal of Cardiovascular Surgery, vol. 26, No. 3, May–June 1985, pp. 217–222.

Heart–Mechanical Assist Device Interaction, JY Kresh; PLM Kerkhof; SM Goldman; and SK Brockman, Trans. Am. Soc. Artif. Intern. Organs, Vol XXXII, 1986, pp. 437–443.

Delayed Recovery of Severaly 'Stunned' Myocardium with the Support of a Left Ventricular Assist Device after Coronary Artery Bypass Graft Surgery, CM Ballantyne MD; MS verani, MD, FACC; HD Short, MD; C Hyatt, BSN, RN; GP Noon, MD, FACC, Journal of the American College of Cardiology, vol. 10, No. 3, September 1987, pp. 710–712.

Long–Term Follow–up of Survivors of Postcardiotomy Circulatory Support, SA Ruzevich; KR Kanter; DG Pennington; MT Swartz; LR McBride; and DT Termuhlen, Trans. Am. Soc. Artif. Intern. Organs, vol. XXXIV, 1988, pp. 116–124.

Extended Clinical Support with an Implantable Left Ventricular Assist Device, MG McGee; SM Parnis; T Nakatani; T Myers; K Dasse; WD Hare; JM Duncan; VL Poirier; and OH Frazier, Trans. Am. Soc. Artif. Intern. Organs, vol XXXV, 1989, pp. 614–616.

Current Status of Cardiac Surgery: A 40–Year Review, WE Richenbacher, MD; JL Myers, MD, FACC; JA Walhausen, MD, FACC, Journal of American College of Cardiology, vol. 14, No. 3, September 1989, pp. 535–544.

Transfemoral Placement of the Left Ventricular Assist Device "Hemopump" During Mechanical Resuscitation, KH Scholz; U Tebbe; M Chemnitius; H Kreuzer; T Schroder; JP Hering; P Uhlig; G Hellige; HJ Grone; R Autschbach; B Schorn; W Ruschewski; and H Dalichau, Thoracic and Cardiovascular Surgeon, vol. 38 (1990) pp. 69–72.

Direct Mechanical Ventricular Actuation for Cardiac Arrest in Humans, MP Anstadt, MD; RL Bartlett, MD; JP Malone, MD, FCCP; and GL Anstadt, VMD; Chest, vol. 100 No. 1, July 1991.

Direct Myocardial Revascularization Without Extracorpoeal Circulation, FJ Benetti, MD; G Naselli, MD; M Wood, MD; and L Geffner, MD, Chest, vol. 100 No. 2, August 1991, pp. 312–316.

Coronary Artery Bypass Without Cardiopulmonary Bypass, Pfister et al, The Annals of Thoracic Surgery, vol. 54 #6 December 1992 pp. 1085–1092.

Coronary Artery Operation Supported by the Hemopump: An Experimental Study on Pig, U Lonn, MD; B Peterzen, MD; H Granfeldt, MD; and H Casimir–Ahn, MD, Ph.D. The Annals of Thoracic Surgery, vol. 58, No. 1, July 1994, pp. 516–523.

Regional Cardiac Wall Immobilization for Open Chest and Closed Chest Coronary Artery Bypass Grafting on the Beating Heart: The 'Octopus' Method, Circulation, vol. 92, No. 8 Supplement 1, I–177 (Oct. 15, 1995).

A Minimally Invasive Surgical Method for Coronary Revascularization–Preliminary Experience in Five Patients, MC Robinson, DR Gross, and W Zeman, Circulation (Oct. 15, 1995) vol. 92, No. 8, I–176.

Coronary Artery Bypass Grafting Without Cardiopulmonary Bypass and Without Interruption of Native Coronary Flow Using a Novel Astamosis Site Restraining Device ("Octopus"), C. Borst et al., Journal of the American College of Cardiology, vol. 27, No. 6, 1356–1364 (May 1996).

Cardiogenic Shock Complicating Acute Myocardial Infarction; the Use of Coronary Angioplasty and the Integration of the New Support Device into Patient Management, GM Gacioch, MD; Stephen G. Ellism, MD, FACC; L Lee, MD; ER Bates, MD, FACC; M Kirsh, MD FACC; JA Walton, MD, FACC; EH Topol, MD, FACC, Journal of the American College of Cardiology, vol. 19, No. 3, Mar. 1, 1992.

Reoperative Coronary Artery Bypass Grafting Without Cardiopulmonary Bypass, WJ Fanning, MD; GS Kakos, MD; and TE Williams, Jr., MD, Ph.D., The Annals of Thoracic Surgery, vol. 55, No. 2, February 1993, pp. 486–489.

Enhanced Preservation of Acutely Ischemic Myocardium with Transeptal Left Ventricular Assist, JD Fonger, MD; Y Zhou, MD; H Matsuura, MD; GS Aldea, MD; and RJ Shemin, MD, The Annals of Thoracic Surgery, vol. 57, No. 3, March 1994, pp. 570–575.

Transcatheter Radiofrequency Ablation of Atrial Tissue Using a Suction Catheter, Th Lavergne et al. PACE, vol. 12, January 1989, Part II, pp. 177–186.

Abstract: "Closed Chest Coronary Artery Bypass With Cardioplegic Arrest in the Dog", Stevens et al. 67th Scientific Sessions.

Placement of Coronary Artery Bypass Graft without Pump Oxygenator, Trapp et al., Journal of the Society of Thoracic Surgeons and The Southern Thoracic Surgical Assn. vol. 19, No. 7 January 1975.

Experimental Videothoracoscopic Cannulation of the Left Atrial Appendix: A Feasible Rapid Approach For Initiating Left Heart Bypass?PF Grändeman; DW Meijer; JJG Bannenberg; R tukkie; and PJ Klopper, Surgical Endoscopy (1993) 7: 511–513.

* cited by examiner

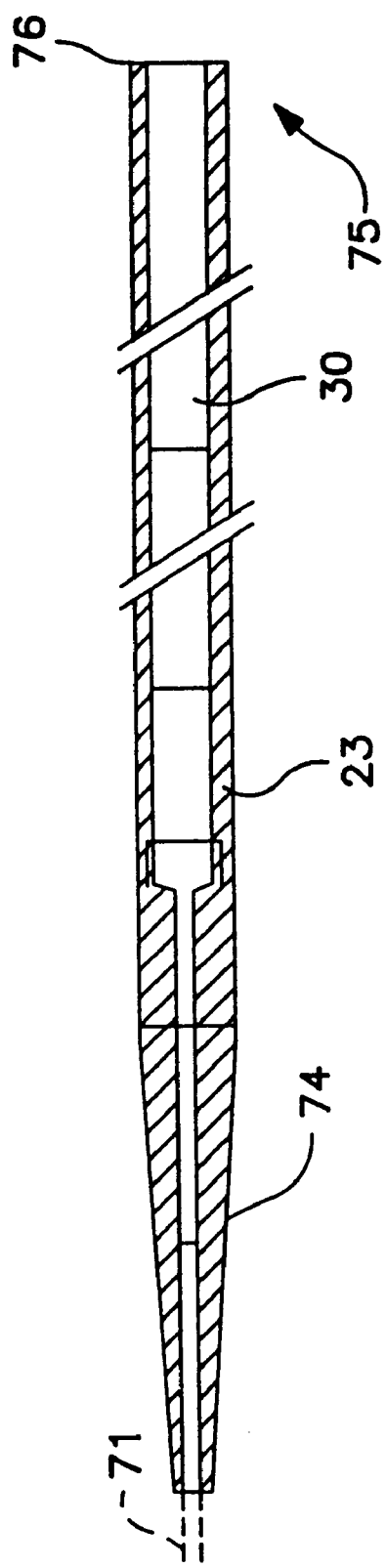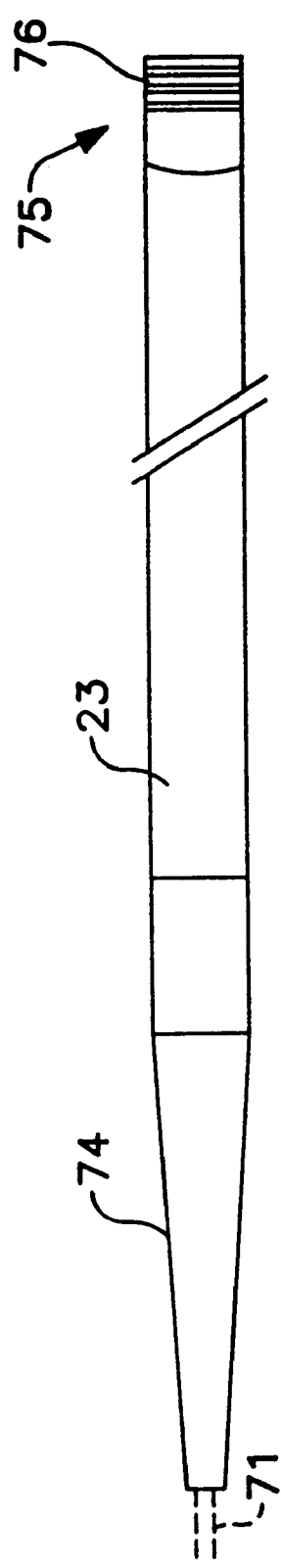
FIG. 6
FIG. 7

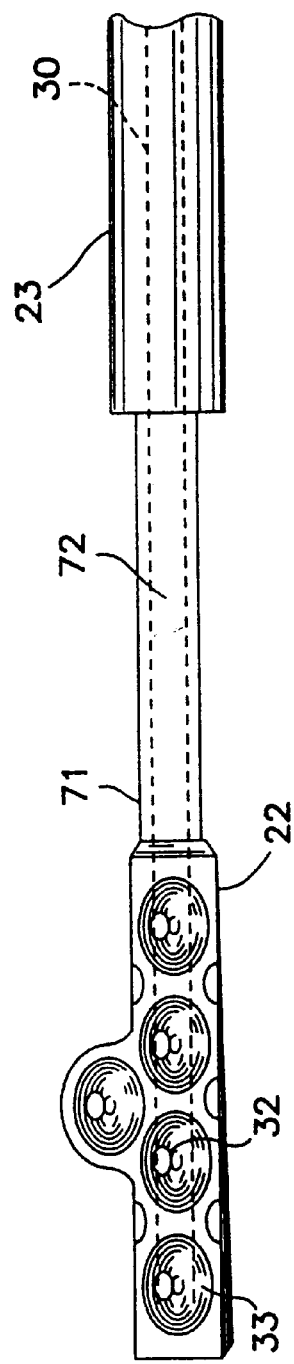
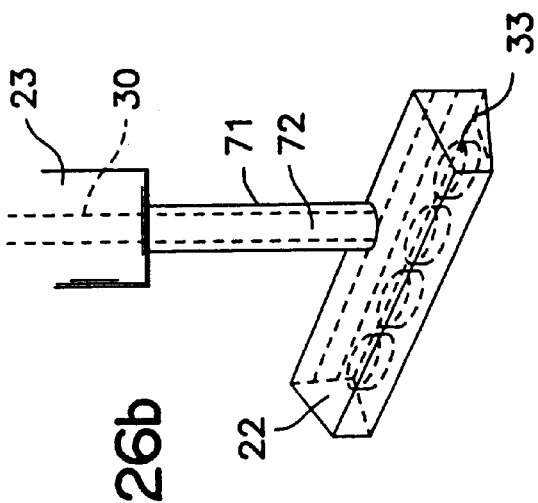
FIG. 26a
FIG. 26b

METHOD AND APPARATUS FOR TEMPORARILY IMMOBILIZING A LOCAL AREA OF TISSUE

RELATED APPLICATION

This is a divisional application claiming priority from application 09/334,531 filed Jun. 19, 1999 of Borst et al. entitled "Method And Apparatus For Temporarily Immobilizing A Local Area Of Tissue", which itself is a divisional application claiming priority from application 08/725,371 filed Oct. 3, 1996 of Borst et al. entitled "Method And Apparatus For Temporarily Immobilizing A Local Area Of Tissue", now U.S. Pat. No. 6,015,378 and which itself is a continuation in part of application 08/531,363 filed Sep. 20, 1995 of Borst et al. entitled "Method And Apparatus For Temporarily Immobilizing A Local Area Of Tissue", now U.S. Pat. No. 5,836,311.

FIELD OF THE INVENTION

The present invention generally relates to surgery on body tissues and organs. More specifically, the present invention relates to a method and apparatus for temporarily immobilizing a local area of tissue subject to motion, such as the heart wall, which permits a surgical procedure to be performed on that local area of tissue.

BACKGROUND OF THE INVENTION

Coronary artery disease remains the leading cause of morbidity and mortality in Western societies. Coronary artery disease is manifested in a number of ways. For example, disease of the coronary arteries can lead to insufficient blood flow to various areas of the heart. This can lead to the discomfort of angina and the risk of ischemia. In severe cases, acute blockage of coronary blood flow can result in irreversible damage to the myocardial tissue including myocardial infarction and the risk of death.

A number of approaches have been developed for treating coronary artery disease. In less severe cases, it is often sufficient to merely treat the symptoms, with pharmaceuticals, or treat the underlying causes of the disease, with lifestyle modification. In more severe cases, the coronary blockage can be treated endovascularly or percutaneously using techniques such as balloon angioplasty, atherectomy, laser ablation, stents, and the like.

In cases where these approaches have failed or are likely to fail, it is often necessary to perform a coronary artery bypass graft procedure. This procedure generally consists of the following steps: First, direct access to the heart is achieved. This is usually done by opening the chest by median sternotomy and spreading the left and right rib cage apart; and opening the pericardial sac to achieve direct access to the heart.

Next, a blood vessel or vessels for use in the graft procedure are mobilized from the patient. This usually entails mobilizing either a mammary artery or a saphenous vein, although other graft vessels may also be used.

Next, a heart-lung or cardiopulmonary bypass is performed. This usually entails arterial and venous cannulation, connecting the bloodstream to a heart-lung machine, cooling the body to about 32 degrees Celsius, cross-clamping of the aorta and cardioplegic perfusion of the coronary arteries to arrest and cool the heart to about 4 degrees Celsius. The arrest or stoppage of the heart is generally required because the constant pumping motion of the beating heart would make surgery upon the heart difficult in some locations and extremely difficult if not impossible in other locations Once cardiac arrest is achieved, then a graft (or grafts) is attached to the relevant portions of a coronary artery (or arteries) followed by weaning from the cardiopulmonary bypass, restarting the heart and decannulation. Finally the chest is closed.

One area which may create difficulties for the patient and extra expense and time for the procedure involves the cardiopulmonary bypass. In a cardiopulmonary bypass all the patient's blood, which normally returns to the right atrium, is diverted to a system which supplies oxygen to the blood and removes carbon dioxide and returns the blood, at sufficient pressure, into the patient's aorta for further distribution into the body. Generally such a system requires several separate components, including an oxygenator, several pumps, a reservoir, a blood temperature control system, filters as well as flow, pressure and temperature sensors.

Problems may develop during cardiopulmonary bypass due to the reaction blood has to non-endothelially lined surfaces, i.e. surfaces unlike those of a blood vessel. In particular, exposure of blood to foreign surfaces results in the activation of virtually all the humoral and cellular components of the inflammatory response, as well as some of the slower reacting specific immune responses. Other complications from cardiopulmonary bypass include loss of red blood cells and platelets due to shear stress damage. In addition, cardiopulmonary bypass requires the use of an anticoagulant, such as heparin. This may, in turn, increase the risk of hemorrhage. Finally cardiopulmonary bypass sometimes necessitates giving additional blood to the patient. The additional blood, if from a source other than the patient, may expose the patient to blood born diseases.

Due to the risks incurred during cardiopulmonary bypass, others have attempted to perform a coronary artery bypass graft procedure without cardiac arrest and cardiopulmonary bypass. For example, Trapp and Bisarya in "Placement of Coronary Artery Bypass Graft Without Pump Oxygenator", Annals Thorac. Surg. Vol. 19, No. 1, (January 1975) pgs. 1–9, immobilized the area of the bypass graft by encircling sutures deep enough to incorporate enough muscle to suspend an area of the heart and prevent damage to the coronary artery. More recently Fanning et al. in "Reoperative Coronary Artery Bypass Grafting Without Cardiopulmonary Bypass", Annals Thorac. Surg. Vol. 55, (Febuary 1993) pgs. 486–489 also reported immobilizing the area of the bypass graft with stabilization sutures.

While these attempts have achieved some success, they generally require enhanced skill of the surgeon to properly create the anastomsis because, even with sutures, the beating heart continues to move in the relevant area more than desired.

SUMMARY OF THE INVENTION

It is thus an object of the present invention to provide a method and apparatus for temporarily immobilizing a local area of tissue, such as an area of a beating heart, without requiring the use of stabilizing sutures.

It is a further object of the present invention to provide a method and apparatus to facilitate performing coronary artery bypass graft surgery on a beating heart.

It is the further object of the present invention to provide a method and apparatus to perform a coronary artery bypass graft without requiring the heart to be arrested or stopped and the patient coupled to a cardiopulmonary bypass machine.

These and other objectives are met by the present invention which comprises a method and apparatus for temporarily immobilizing a local area of tissue. In particular, the present invention provides a method and apparatus for temporarily immobilizing a local area of heart tissue to thereby permit surgery on a coronary vessel in that area without significant deterioration of the pumping function of the beating heart. The local area of heart tissue is immobilized to a degree sufficient to permit minimally invasive or micro-surgery on that area of the heart. The present invention features a suction device to accomplish the immobilization. The suction device is coupled to a source of negative pressure. The suction device has a series of suction ports on one surface. Suction through the device causes suction to be maintained at the ports. The device further is shaped to conform to the surface of the heart. Thus, when the device is placed on the surface of the heart and suction is created, the suction through the ports engages the surface of the heart. The suction device is further fixed or immobilized to a stationary object, such as an operating table or a sternal or rib retractor. Thus, the local area of the heart near the suction device is temporarily fixed or immobilized relative to the stationary object while suction is maintained. In such a fashion, the coronary artery may be immobilized even though the heart itself is still beating so that a bypass graft may be connected to the coronary artery. In addition the suction device may be used in either a conventional, open-chest environment or in a minimally-invasive environment, e.g. endoscopic.

BRIEF DESCRIPTION OF THE DRAWINGS

The foregoing and other aspects of the present invention will best be appreciated with reference to the detailed description of the invention in conjunction with the accompanying drawings, wherein:

FIG. 6 is a longitudinal sectional view of the suction arm used in the present invention.

FIG. 7 is a plan view of the suction arm used in the present invention.

FIG. 26A is a view of the bottom of an alternate embodiment of a suction paddle used in the immobilizing device.

FIG. 26B is a perspective view of a further alternate embodiment of a suction paddle used in the immobilizing device.

The drawings are not necessarily to scale.

DETAILED DESCRIPTION OF THE PREFERRED EMBODIMENT

Figure 1:
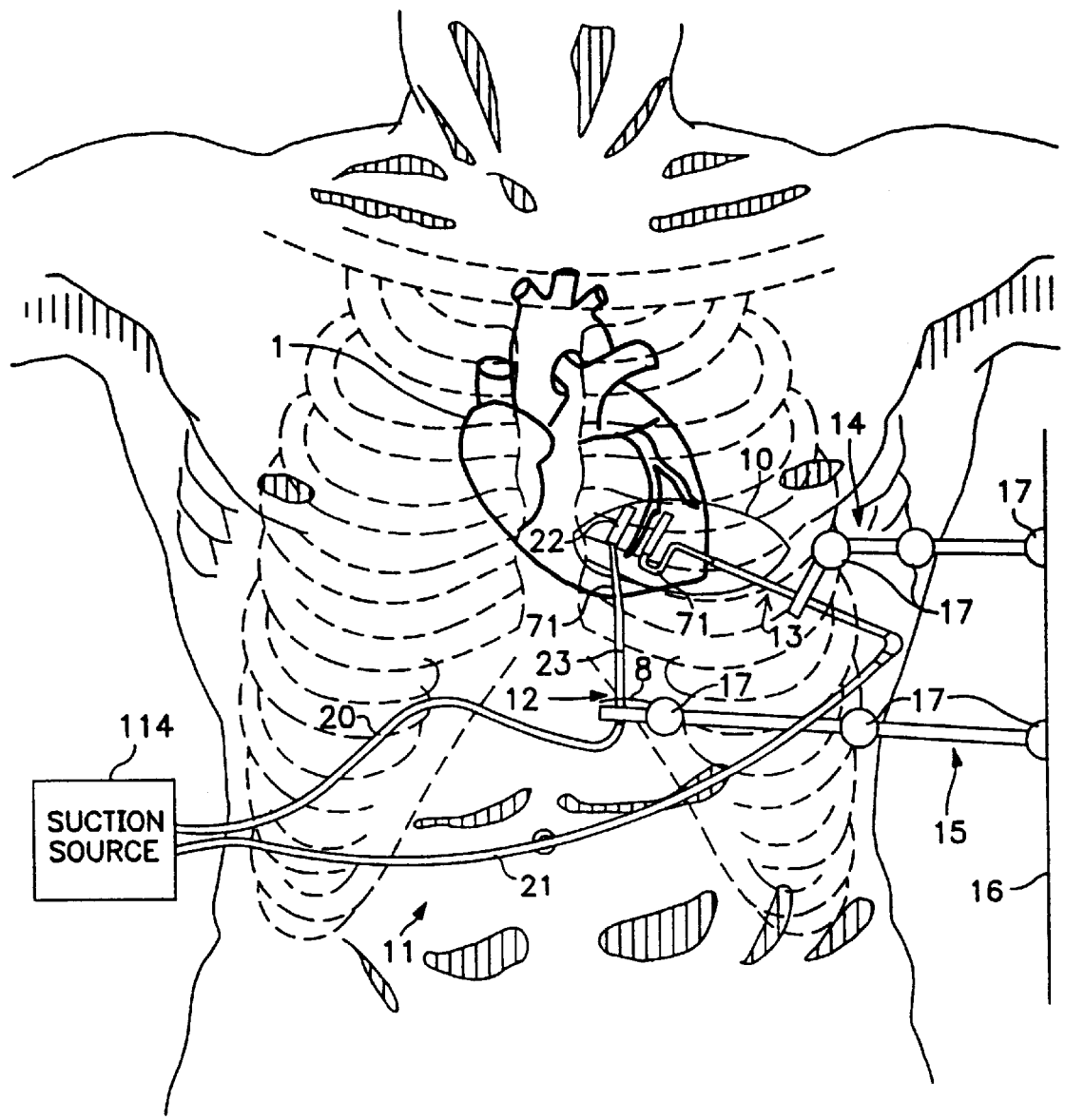
FIG. 1 is a plan view of the device being used to temporarily immobilize a local area of heart tissue in which access to the heart is achieved through a mini-thoracotomy.

FIG. 1 is a view of the immobilizing device 11 being used to temporarily immobilize an area of heart tissue. In the preferred embodiment, surgical access to the local area of heart tissue is achieved through a mini-thoracotomy, preferably performed within either the fourth or fifth intercostal space. An incision 10 of approximately 10 centimeters is made into chest cavity between the ribs (seen here in phantom.) The rib cartilage may be temporarily removed and the ribs surrounding the incision slightly spread apart using a retractor (not shown) to provide adequate surgical access to the mammary artery and the heart. As seen, a pair of suction devices 12, 13 are introduced. The first suction device 12 is introduced through a small stab wound 8 in between the ribs approximately 10 cm. below incision 10. This stab wound is made in any acceptable manner. Incidentally, once the surgery has been completed, the stab wound may be used for the thorax drain after the closure of the chest. As discussed below with reference to FIG. 19, the suction device has a covering 180, made from latex rubber, over the distal end when it penetrates the chest wall in order to avoid blood and tissue from entering the suction ports and block suction apertures. Once suction device is introduced, covering 180 is removed and the distal end is positioned onto heart. The second suction device 13 is introduced through incision 10 onto the surface of the heart. As seen, the distal end of each suction device is ultimately positioned in the local area of heart tissue to be immobilized, i.e. on either side of a coronary artery upon which a graft is to be made.

As seen, suction devices 12,13 are secured using securing devices 14, 15 respectively to a stationary object, such as surgical table 16. Of course other objects besides the surgical table may be used as a stationary object, including the floor, ceiling or even the patient, such as a portion of the skeletal system of the patient, e.g. the sternum. In the preferred embodiment, each securing device 14,15 is a variable friction arm, model no. 244 available from Manfrotto Nord, Inc. of Zona Industriale di Villapaiera, I-32032 Feltre BL, Italy. Each securing device 14, 15 has a series of elbow joints 17 which may be locked in position. Thus the securing device permits the suction device to be locked into any position desired within three-dimensional space. Although not show, each securing device (or each suction device or both) may also be interconnected such that a truss type structure is created and the entire stiffness or rigidity of the immobilizing device 11 is improved.

Suction devices 12,13 are coupled to a suction source 114 through lines 20, 21. Suction source 114 is preferably the standard suction available in the operating room and coupled to the devices with a two liter buffer flask (not shown) for each device. Suction is provided at a negative pressure of between 200–600 mm Hg with 400 mm Hg preferred. As seen, each suction device has essentially two portions, a paddle 22 and an arm 23. FIGS. 2 and 3 detail suction devices 12 and 13 respectively.

Figure 2A:
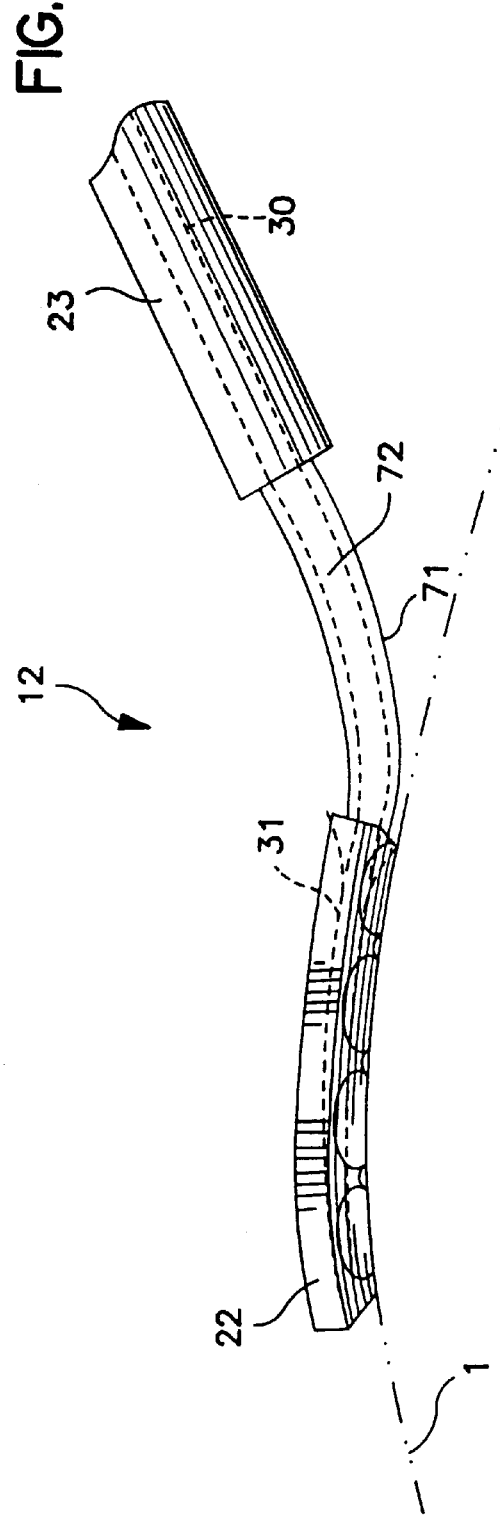
FIGS. 2a and 2b depict a first type of suction device shown in use in FIG. 1.
Figure 2B:
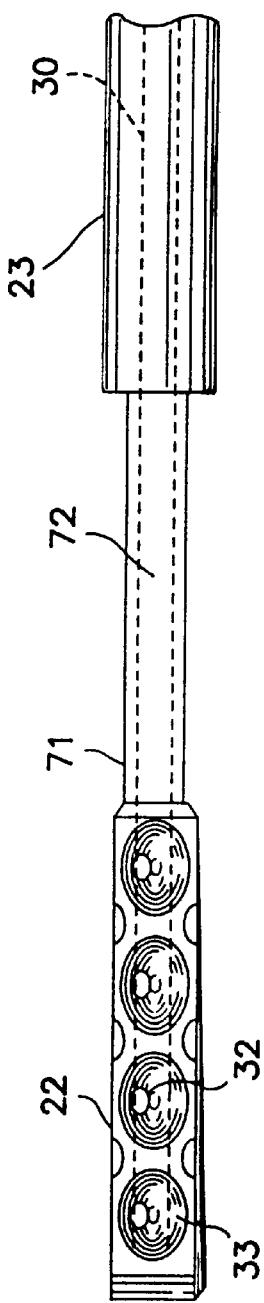

Turning now to FIGS. 2a and 2b, FIG. 2a is a side view of a suction device 12 showing its placement against the outline of a heart. As seen, the distal end of suction device comprises a paddle 22 and arm 23 coupled together by a continuous hinge or neck 71. Paddle 22 has a generally planar surface which conforms generally to the curvature of a heart 1, shown here in outline. In the preferred embodiment, suction arm 23 is coupled to suction paddle 22 such that suction paddle 22 may be rotated or bent to achieve the desired orientation relative to arm 23. This is accomplished by neck 71. Neck 71 is fashioned to be relatively bendable, that is to be bent by hand into the desired orientation, as opposed to paddle 22 and arm 23, which are rigid. In the preferred embodiment suction paddle 22 and suction arm 23 are constructed of stainless steel 316, while neck 71 is constructed of stainless steel 321. Of course other means may be provided to permit paddle 22 to move or rotate relative to arm 23 other than making neck 71 to be malleable by hand, such as a locking hinge as well as a remotely actuable joint, as is well known in the art. See for example, U.S. Pat. No. 5,374,277 of Hassler, incorporated herein by reference. A remotely actuable hinge is believed particularly advantageous for a suction device used endoscopically. In an alternate embodiment paddle may be fixed in a rigid orientation relative to arm. As seen, arm 23 has a suction lumen 30 therethrough which communicates with a suction conduit 31 in paddle 22 through neck lumen 72. Suction conduit 31 in paddle 22 further communicates through suction hole 32 (best seen in FIG. 2b) to suction port 33.

FIG. 2b is a view of the bottom of suction device 12. As seen, in the preferred embodiment four suction ports 33 in a row are featured, although the specific or exact number and position used may vary. Each suction port 33 has a suction aperture 32, each of which are preferably located at a position off-center from suction port 33. Suction apertures 32 are positioned off center from suction ports 33 so that if a large upwelling of tissue is caused by the suction (which may occur as a blister or bell-shaped curve) the tissue will not immediately close off the suction by obstructing suction aperture 32, as it would if the aperture were in the center of suction port 33. In addition, each suction aperture 32 has a much smaller diameter as compared to the diameter of suction port 33. This creates a high resistance pathway between suction port 33 and suction conduit 31 which permits the loss of a tissue-to-port seal in one suction port (and thus loss of fixation of the suction port to the tissue) to not also cause a precipitous pressure drop in the remainder of the suction ports. In the preferred embodiment suction aperture 32 has a diameter of 2 mm and suction port 33 has a diameter of 6 mm. As can be seen through a comparison between FIGS. 2A and 2B the relatively straight sided suction ports define a generally planar surface through the ends of each port.

Figure 3A:
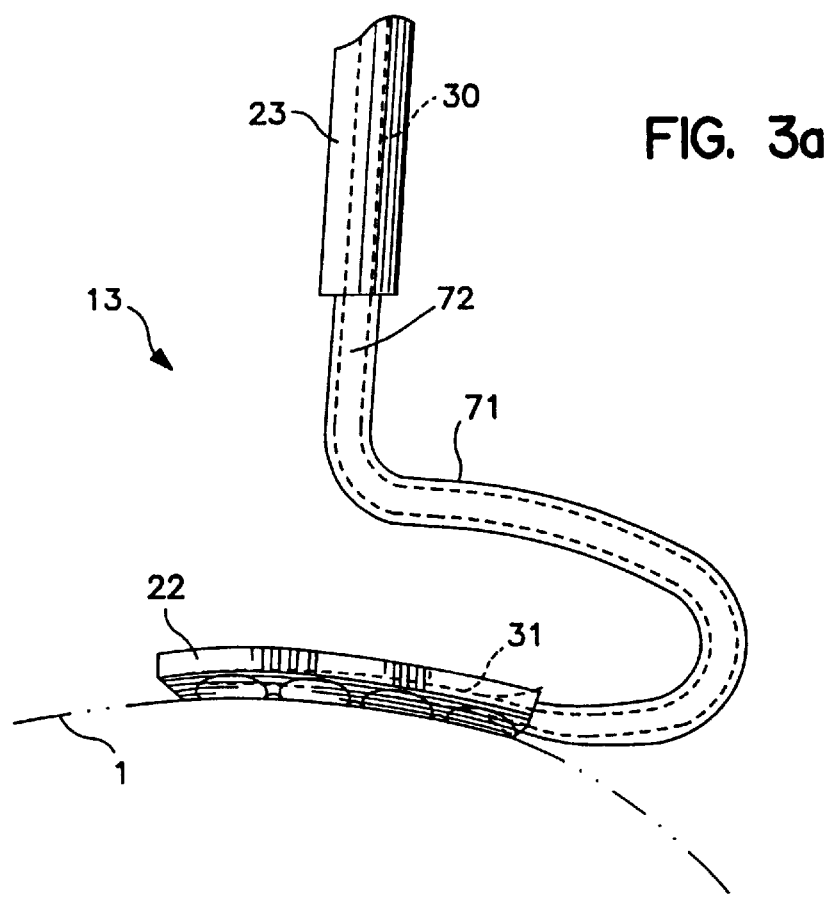
FIGS. 3a and 3b depict a second type of suction device shown in use in FIG. 1.
Figure 3B:
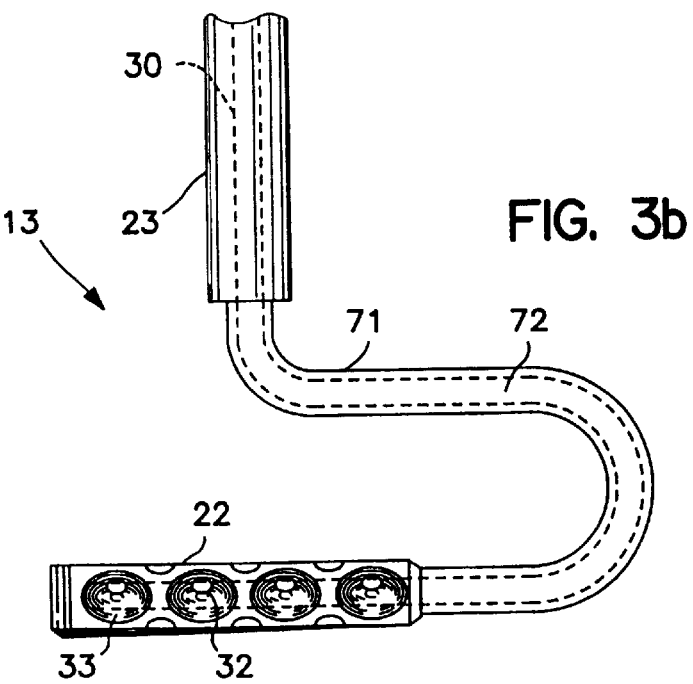

Turning now to FIGS. 3a and 3b, FIG. 3a is a side view of a suction device 13 shown in FIG. 1. As seen, the distal end of suction device 13 comprises paddle 22 and arm 23 coupled together by a continuous hinge or neck 71. Paddle 22 has a generally planar surface which conforms generally to the curvature of a heart 1. In the preferred embodiment, suction arm 23 is coupled to suction paddle 22 such that suction paddle 22 may be rotated or bent along any of the three axes to achieve the desired orientation relative to arm 23. This is accomplished by neck 71. Neck 71 is substantially similar to that discussed in FIG. 2a but for the fact that suction device 13 has suction paddle 22 at an angled orientation to suction arm 23. In the preferred embodiment suction paddle 22 of suction device 13 is perpendicular to suction arm 23, although other angular orientations may be used.

FIG. 3b is a view of the bottom of suction device 13. As seen, in the preferred embodiment suction paddle 22 of suction device 13 is substantially similar to that described in FIG. 2b. In the preferred embodiment suction aperture 32 has a diameter of 2 mm and suction port 33 has a diameter of 6 mm.

Figure 4:
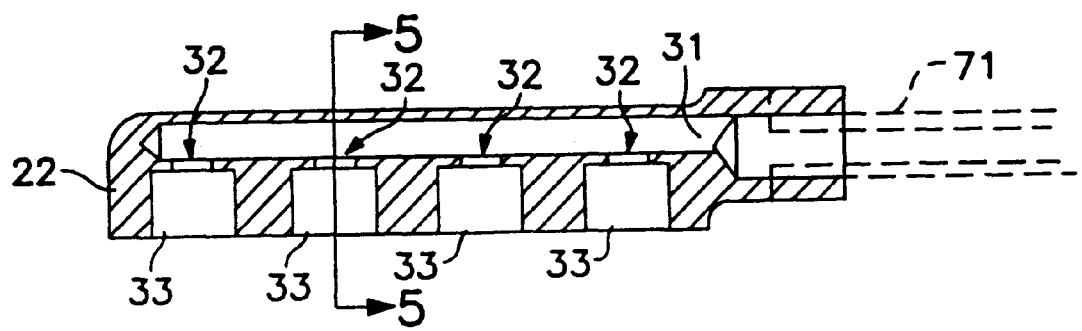
FIG. 4 is a longitudinal sectional view of the suction paddle used in the present invention.

FIG. 4 is a longitudinal cross-sectional view of suction paddle 22 used in immobilizing device 11. As seen, paddle 22 has a series of suction ports 33 each of which is connected to suction conduit 31 through a suction aperture 32. Each suction port 33 has generally straight, cylindrical sides. Of course other configurations may be used, such as cone-shaped suction ports, dome-shaped suction ports, etc. As can be seen through this FIG. it is the bottoms or ends themselves of the suction ports define a generally planar surface through the ends of each port along the bottom surface of the paddle. Moreover, although shown here as conjoined or defining a continuous surface, suction ports may be further arranged such that they are each separate and distinct from one another, but which would still define a planar surface along through their ends along the bottom of the paddle.

Figure 5:
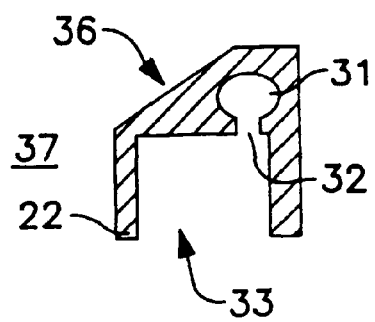
FIG. 5 is a cross-sectional view of the suction paddle used in the present invention taken along the line 5—5 of FIG. 4.

FIG. 5 is a cross-sectional view of the suction paddle 22 taken along the line 5—5 of FIG. 4. As seen, suction port 33 is connected to suction conduit 31 through suction aperture 32. Suction paddle 22 has a canted or slanted surface 36 at the top. Through this type of surface, area 37 may be better accessed for performing surgical procedures.

FIG. 6 is a longitudinal cross-sectional view of suction arm 23. Distal end 71 of suction arm 23 has neck 71 (not shown in this FIG.) fixed thereto. As seen, arm 23 has a suction lumen 30 therethrough which communicates with suction conduit 31 in paddle 22 through neck lumen 72 of neck 71 (shown in phantom in this FIG.). As seen in FIG. 7, which is a plan view of suction arm 23, proximal end 75 has a series of knurled ridges 76 to facilitate coupling a suction line coming from suction source (not shown in this FIG) to suction arm 23.

Figure 8:
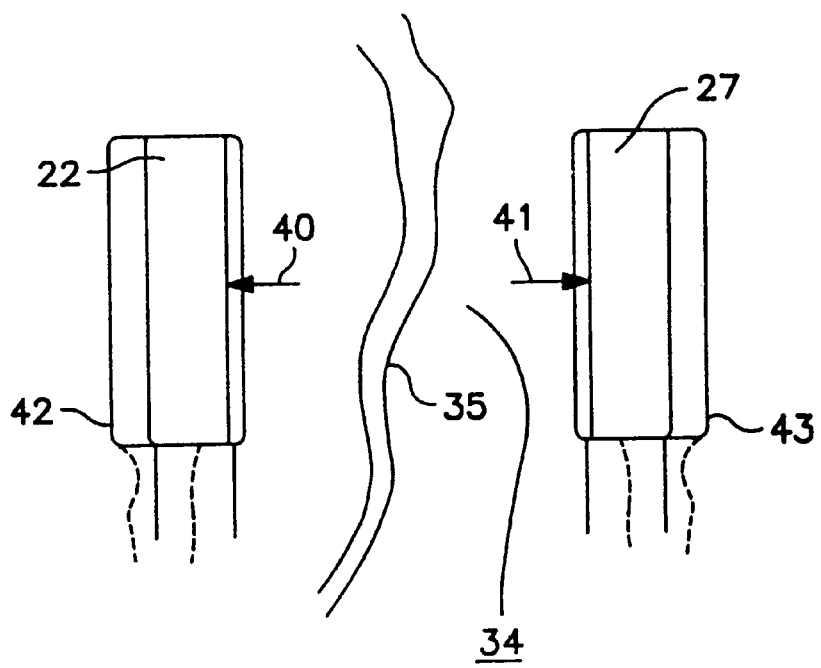
FIG. 8 is a detailed view of a pair of suction devices being positioned on a heart and spread apart.

FIG. 8 is a detailed view of a pair of suction devices 12, 13 being positioned on a heart and spread apart. As seen, paddles 22, 27 of each device generally are placed in the area 34 in which temporary immobilization of the heart tissue is desired. When used for a coronary bypass graft, area 34 typically will have a coronary artery 35 running therethrough. Area 34 is between paddles 22, 27. Once placed about area 34, suction is then created in the suction ports (not shown in this view.) Through the suction, the device then is fixed to or grabs hold of the heart tissue.

Once the suction is created and the paddles are secured to the heart tissue, each of the suction devices are then spread slightly apart as shown by the arrows 40, 41 to the positions shown as 42, 43. The effect of this spreading apart is to cause a tension to be created in the area 34 of the heart tissue between the paddles. The tension causes the area 34 to be further immobilized, and in particular in the Z-direction, i.e. in the direction normal to the plane defined by the surface of the heart. This is represented in FIGS. 9 and 10.

Figure 9:
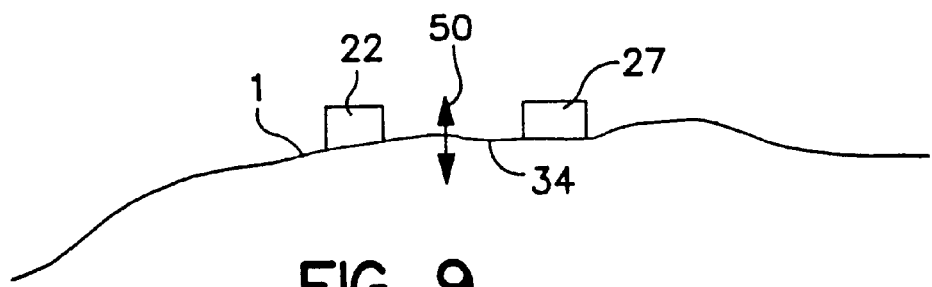
FIGS. 9 and 10 show the effect of the spread-apart motion depicted in FIG. 8.
Figure 10:
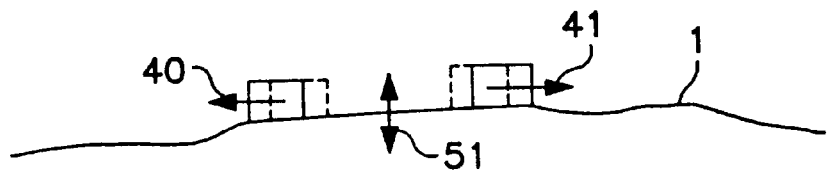

As seen in FIG. 9, the area of heart tissue between the paddles, even with the placement of the paddles, still has some vertical motion, shown here as arrow 50. When paddles 22, 27 are slightly spread apart to cause a tension in that area 34 of tissue between the paddles, as depicted in FIG. 10, then the amount of movement in the area 34 between the paddles 22, 27 due to the tension is further decreased, especially in the Z-direction, i.e. the direction perpendicular to the surface of the heart 1. Once the paddles 22, 27 are thus positioned and secured and the area of the tissue is temporarily immobilized, the coronary artery in that area may be operated upon.

In the preferred embodiment, the anastomosis of the coronary artery may be accomplished through any acceptable end-to-side or side-to-side technique. Of course, other methods of performing the anastomosis may be used, such as those methods which may be performed endoscopically.

Figure 12:
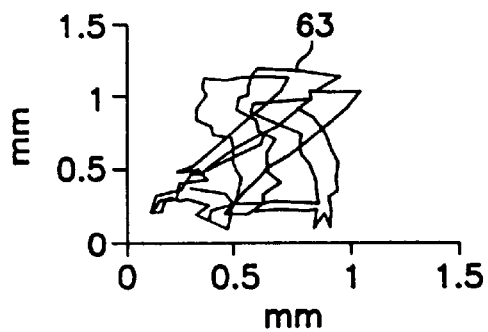
FIG. 12 is an enlarged portion of FIG. 11 depicting the motion of the same point on heart tissue when the suction devices are used.
Figure 11:
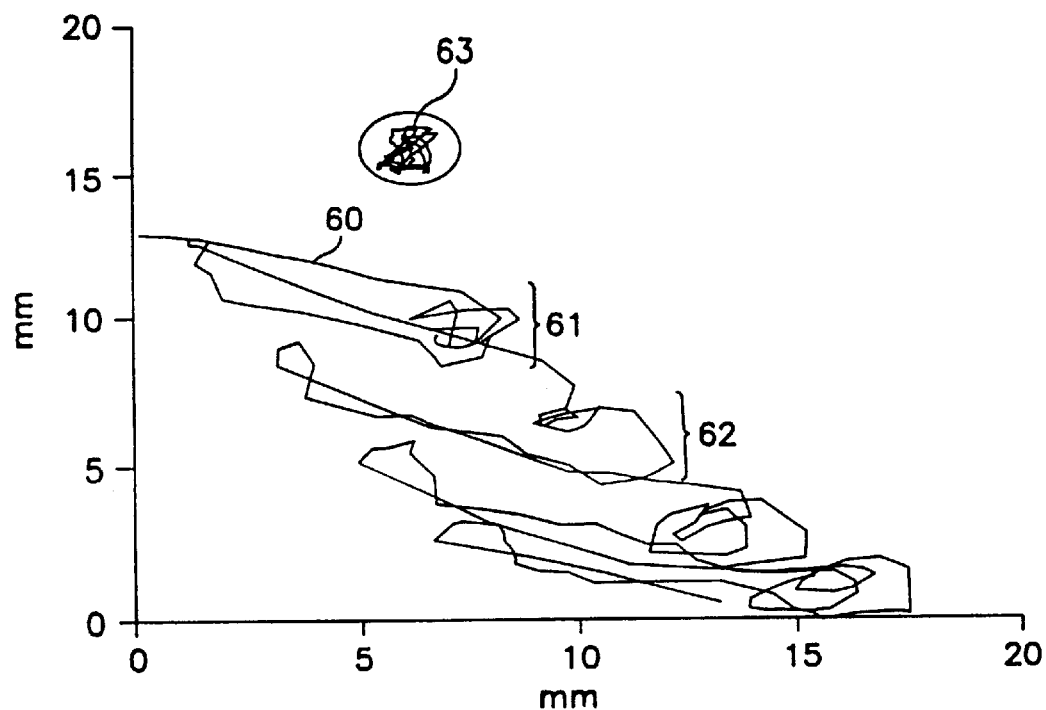
FIG. 11 is an example of the motion in the plane parallel to the surface of the heart of a point on heart tissue during one half respiratory cycle when the heart is unrestrained and also depicting the motion of the same point on heart tissue when the suction devices are used.

FIG. 11 is an example of the motion in the plane parallel to the surface of the heart of a point on heart tissue during one half respiratory cycle when the heart is unrestrained and also depicting the motion of the same point on heart tissue when the suction devices are used. Line 60 is a tracing of the motion of a point of tissue on the cardiac surface. As seen by line 60, a point on the cardiac surface moves approximately 15 mm in each direction. Generally, each loop of movement depicts the motion of the beating heart within one cardiac cycle. Thus, loop 61 occurs due to one cardiac cycle. Loop 62 occurs due to the next cardiac cycle, but the entire heart has shifted in location somewhat due to the inflation or deflation of the lungs associated with respiration. Line 63 shows the motion of the same point of heart tissue when the suction device is placed near the area and the heart wall is immobilized by the present invention. As seen, the present invention functions to minimize heart wall movement in that area to approximately 1 mm in each direction. This is best seen in FIG. 12 which is an enlarged portion of FIG. 11 and in particular line 63. As seen, through the use of the present invention, heart wall movement has been decreased to only slightly more than 1 mm. Decreased to an amount in the area of the suction devices such that the still-beating heart may be operated upon in that area using an endoscope or any other method of minimally invasive surgery.

Figure 13:
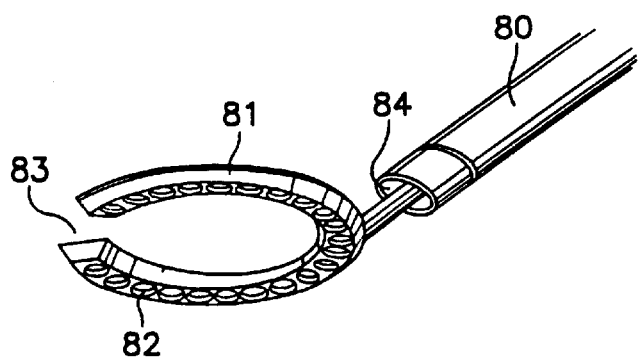
FIG. 13 is an alternate embodiment of the present invention.

FIG. 13 is an alternate embodiment of the present invention. As seen, the embodiment of FIG. 13 comprises a suction sleeve 80 which is coupled to an annular suction head 81 via a ball bearing joint 84. Ball bearing joint 84 may be provided so as to permit remote actuation of the suction head 81 from a position outside the chest. The suction head 81 has a series of suction ports 82 located along a first planar surface. In the embodiment shown the planar surface upon which the suction ports 82 are located is conical in shape, although other types of planar surface may be used, such as frusto-conical for example. The suction head 81 may be constructed such that each half of the device is coupled to a separate suction source. Through such a configuration, if one-half of the suction head 81 were to lose contact with the surface, the other one-half of the suction head 81 could maintain capture. The suction sleeve 80 is used as described above. That is the suction sleeve 80 itself is coupled to a suction source (not shown but the same as suction source 114) and is fixed or immobilized to a stationary point, such as the operating table or a retractor (also not shown.) Suction through the suction source and the suction sleeve 80 then causes the suction ports 82 to suck upon the heart tissue. Through this configuration, then, the heart tissue in the center of suction sleeve is immobilized. Interruption or opening 83 permits suction head 81 to be fixed to heart tissue while permitting a blood vessel to be grafted. In particular, if a mammary artery has been grafted end-to-side to a coronary artery, then the opening 83 permits the suction head 81 to be removed from around the grafted artery.

Figure 14:
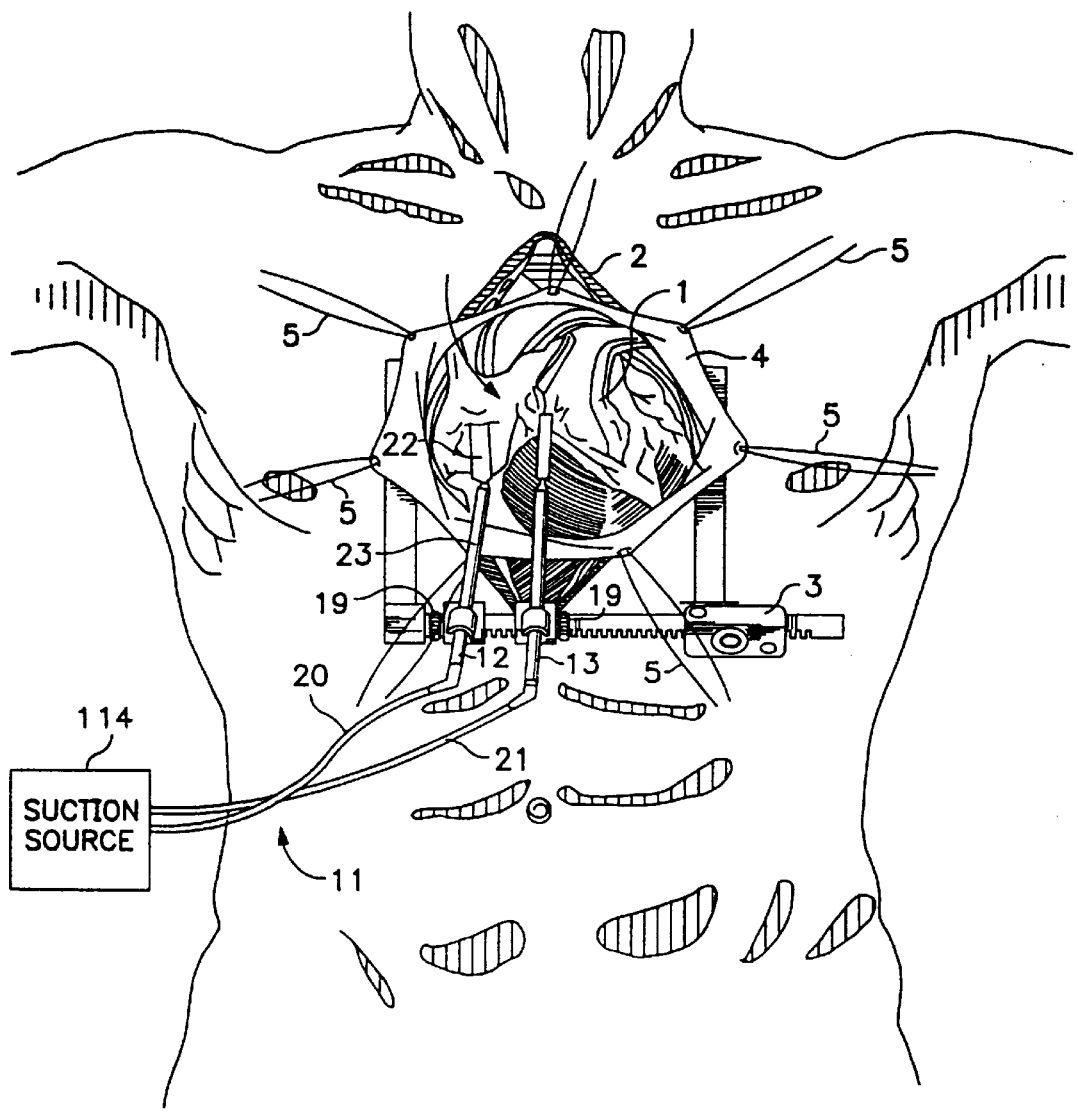
FIG. 14 is a plan view of the device being used to temporarily immobilize a local area of heart tissue in which access to the heart is achieved through a median sternotomy.

FIG. 14 is a view of the device being used to temporarily immobilize a local area of heart tissue using an alternative access procedure to the preferred mini-thoracotomy. In particular heart 1 is exposed with an incision 2 through the patient's sternum and the chest is spread apart by a retractor 3 to provide access to the heart 1. Access to the heart 1 is further effected by retraction of the pericardium 4 in the area of the heart 1 which is to be operated on. As shown pericardial retraction is accomplished through sutures 5.

As seen, the immobilizing device 11 comprises a pair of suction devices 12, 13 and a suction source 114. Suction devices 12,13 are secured to patient be securing each to retractor 3 through a pair of clamps 19. Of course suction devices 12, 13 may also be secured to the operating table (not shown in this FIG. but using a securing device as described above.) Suction devices are coupled to suction source 114 through lines 20, 21. Suction source 114 is preferably the standard suction available in the operating room and coupled to the devices with a two liter buffer flask (not shown) for each device. Suction is provided at a negative pressure of between 200–600 mm Hg with 400 mm Hg preferred. As seen, each suction device has essentially two portions, a paddle 22 and an arm 23.

Figure 15:
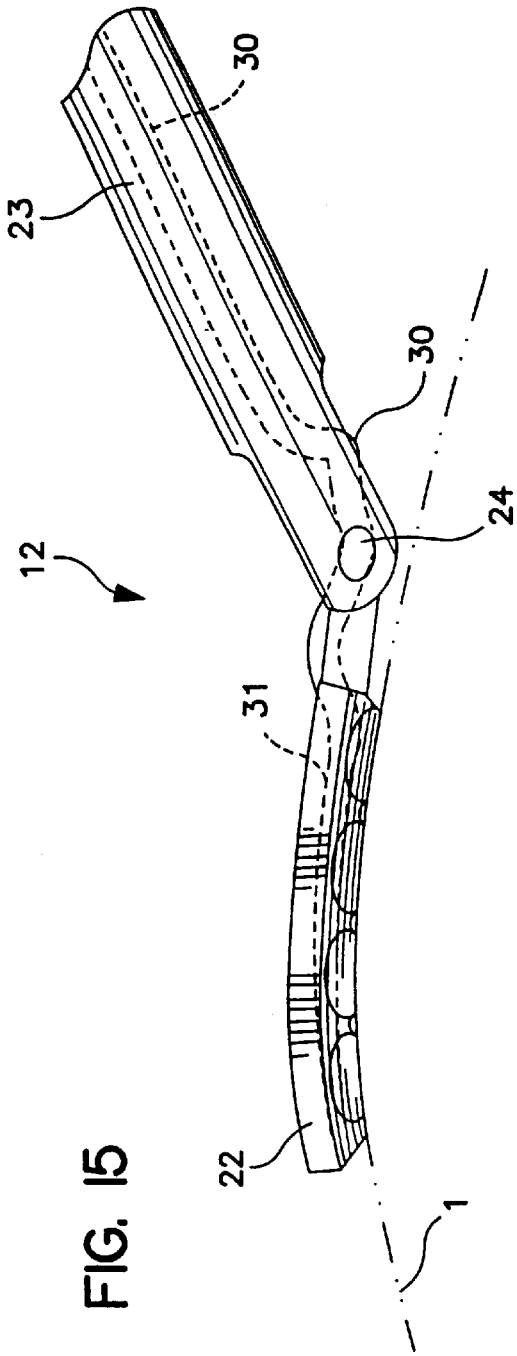
FIG. 15 is a side view of an alternate embodiment of the present invention, shown placed against the surface of the heart.

Turning now to FIG. 15 which is a side view of an alternate embodiment of suction device 12 showing its placement against the outline of a heart. As seen, the distal end of suction device comprises a paddle 22 and arm 23. Paddle 22 has a generally planar surface which conforms generally to the curvature of a heart 1, shown here in outline. The paddle 22 is coupled to arm 23 through a pin 24. The pin 24 permits the paddle 22 to be swiveled to the preferred angle relative to arm 23. As seen, arm 23 has a suction lumen 30 therethrough which communicates with a suction conduit 31 in paddle 22. Suction conduit 31, in turn, communicates through suction aperture 32 (best seen in FIG. 4) to suction port 33.

Figure 16:
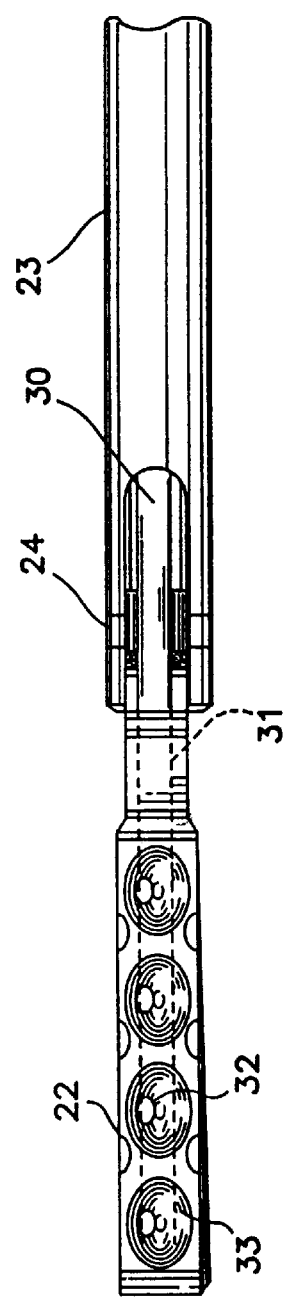
FIG. 16 is a bottom view of the alternate embodiment of the present invention device shown in FIG. 15.

FIG. 16 is a view of the bottom of suction device 12 shown in FIG. 15. As seen, four suction ports 33 in a row are featured, although the specific or exact number and position used may vary.

Figure 17:
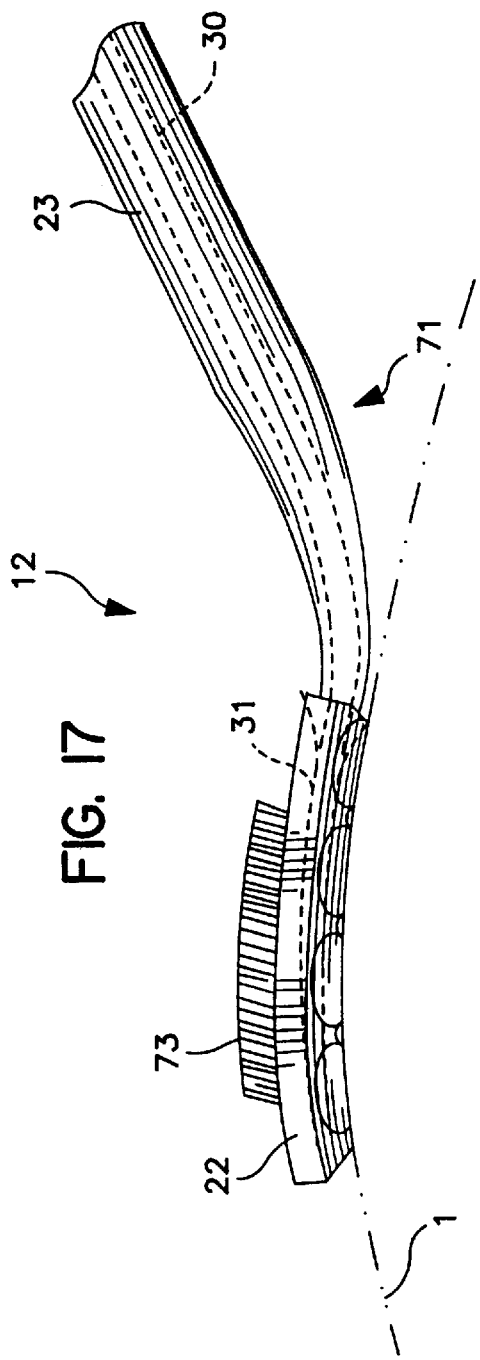
FIG. 17 is a side view of a further alternate embodiment of the present invention, shown placed against the surface of the heart.

FIG. 17 is a further alternate embodiment of a suction device 12 showing its placement against the outline of a heart. As seen, suction device 12 is substantially similar to that shown and described in FIG. 2, but for the addition of suture coil 73. Suture coil 73 is a tightly wound spring fixed to the top surface of suction paddle 22. Further temporary stabilization of the coronary anastomosis site may be achieved, if desired, by catching epicardial flaps with light traction sutures. Suture coil 73 permits these and any other sutures to be temporarily fixed in place by wedging the suture between within suture coil 73, as is known in the art.

Figure 18:
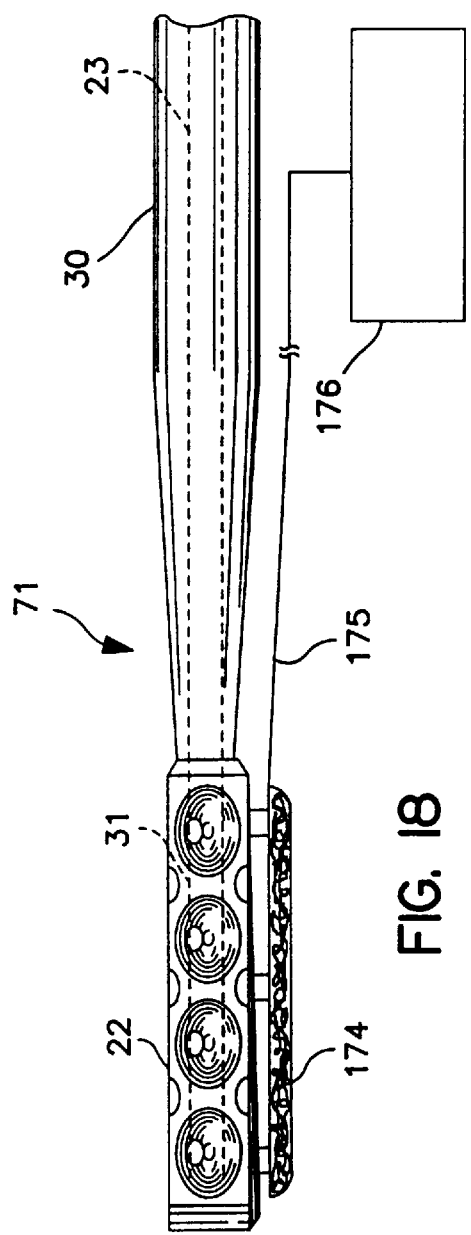
FIG. 18 is a bottom view of still further alternate embodiment of the present invention.

FIG. 18 is a bottom view of a further alternate embodiment of suction device 12. As seen, suction device 12 is substantially similar to that shown and described in FIG. 2, but for the addition of electrode 174 along a side of suction paddle 22. Electrode 174 is coupled by lead 175 to pulse generator 176. Electrode 174, lead 175 and pulse generator 176 may be provided according to well know methods and materials so as to permit the heart to be paced, cardioverted or defibrillated while suction device 12 is fixed to the surface of the heart.

Figure 19:
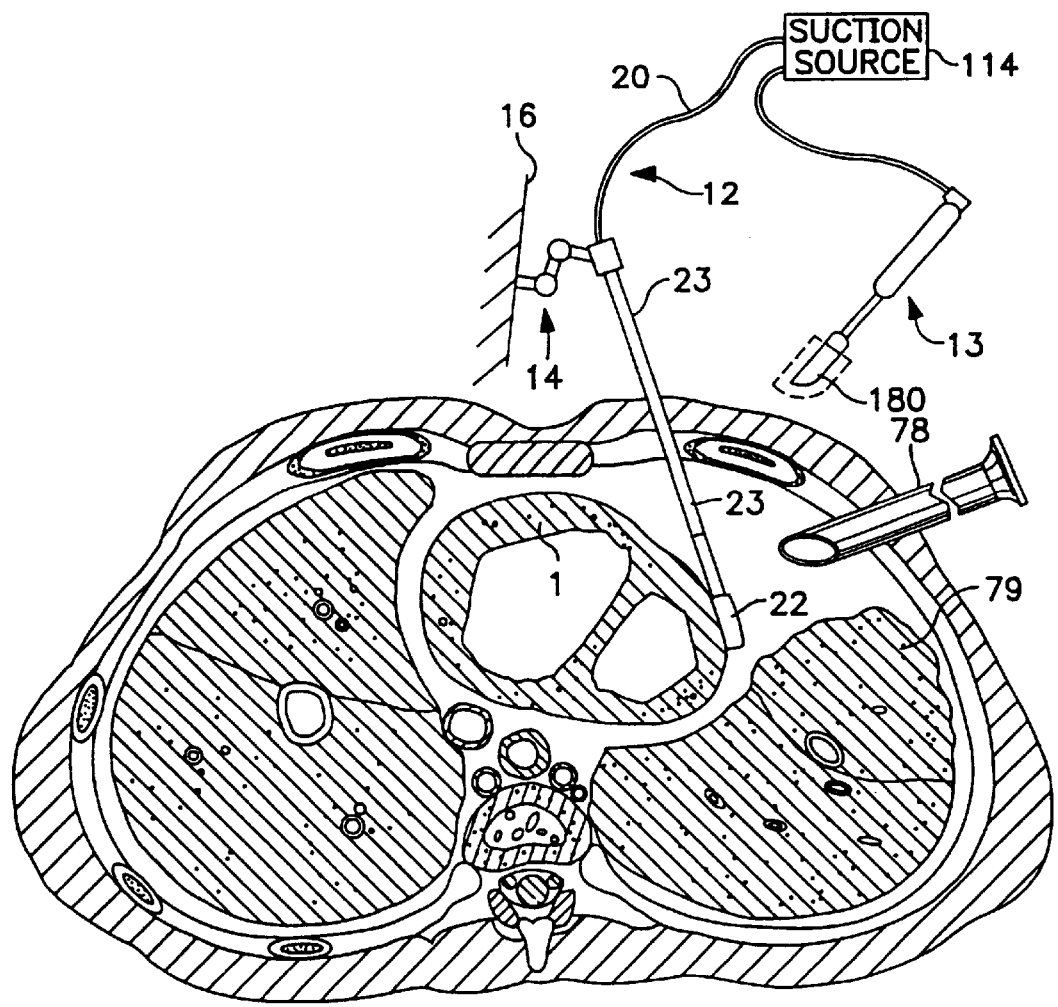
FIG. 19 is a cross-sectional view of a body showing an alternative method of achieving access to the surface of the heart, and in particular of achieving such access using minimally invasive trocars.

FIG. 19 is a cross-sectional view of a body showing an alternate method of achieving access to a surface of the heart and using the present invention to immobilize an area of tissue. As seen suction device 12 is introduced through a first stab wound. As discussed above, suction arm 23 of device 12 is secured by securing device 14 to a stationary object, such as operating table 16. A second suction device may also be introduced through a second stab wound to securely immobilize a local area of tissue. Each suction device has a covering 180, made from latex rubber, over the distal end when it penetrates the chest wall in order to avoid blood and tissue from entering the suction ports and block suction apertures. Two or more additional surgical trocars 78 may be introduced to permit endoscopy and surgical access to heart 1. In addition the left lung 79 may also be partially collapsed so as to provide an unencumbered area in which to manipulate the surgical instruments.

Figure 20A:
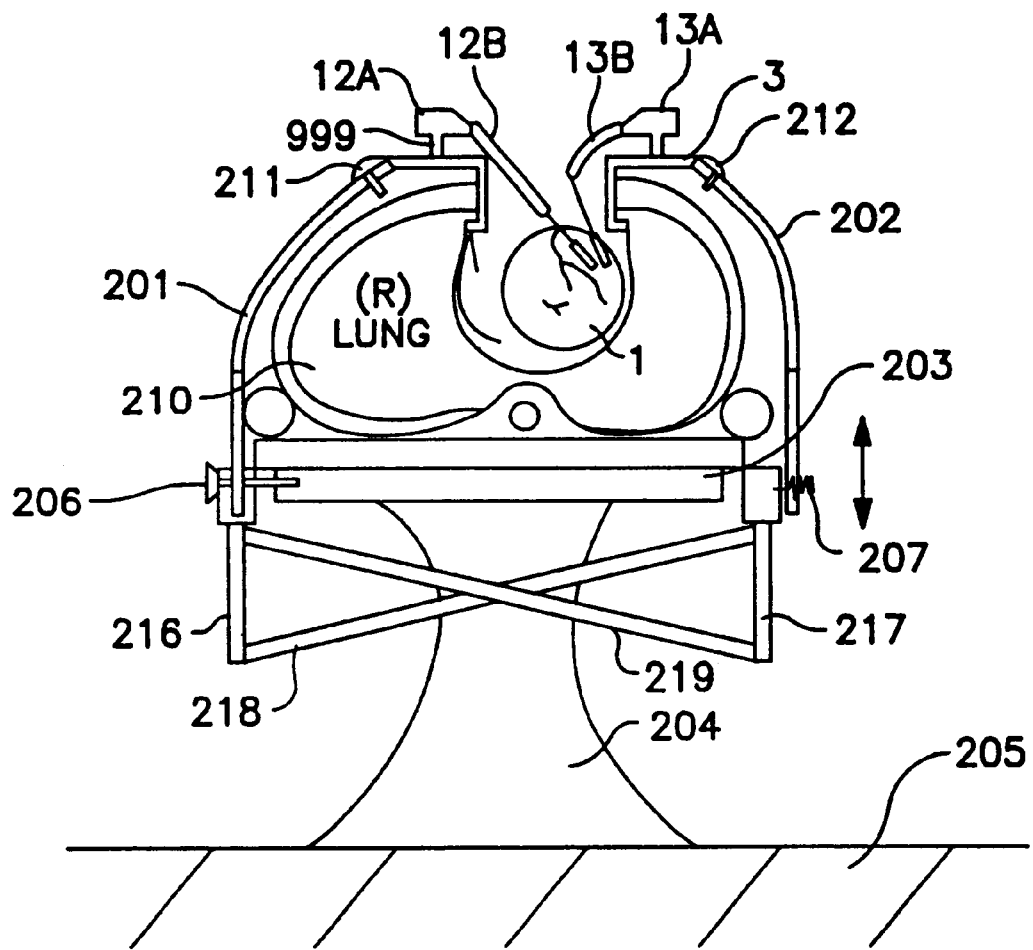
FIG. 20A is a cross-sectional view of a body showing an alternate embodiment of the present invention, and in particular, an alternate embodiment of the securing device.

FIG. 20A is a cross-sectional view of a body showing an alternate embodiment of the present invention, and in particular, an alternate embodiment of the securing device. In this embodiment, securing device comprises a pair of anchors 201, 202 which are attached to surgical table 203. As seen, surgical table is attached by pedestal 204 to the floor 205. Each anchor is attached on either side of the table using a pair of fasteners 206, 207. In the preferred embodiment, fasteners are a pair of screws which couple with longitudinal slots within each anchor to permit the anchors to be adjusted both in an inward and outward direction as well as up and down, as shown by the arrows. As seen, anchors are designed to follow the contour of patient 210 to thereby provide a smooth surface over which a surgeon may operate. Each anchor is attached to retractor 3 by fasteners 211, 212. On the retractor 3 a mounting rail 999 is attached, best seen in FIG. 20B discussed below. Attached in turn to mounting rail is a pair of slip-grip type holders 12A, 13A or any other holder which permits an object to be quickly but securely mounted or removed, and mounted in turn to holders are a pair of suction devices 12B, 13B as has been already previously discussed above. In the preferred embodiment, each anchor is a strip of biocompatible metal, such as stainless steel, approximately 5–8 centimeters in width and 0.6–0.8 centimeters in thickness. As seen positioned at the bottom of anchors is a truss. In particular each anchor has fixed to it a descending member 216, 217, each of which are linked together by a pair of cross-braces 218, 219. Cross-braces may or may not be coupled together at their center points. As can be appreciated, through this truss construction the stability of anchors and thus the suction devices mounted thereto is increased.

Figure 20B:
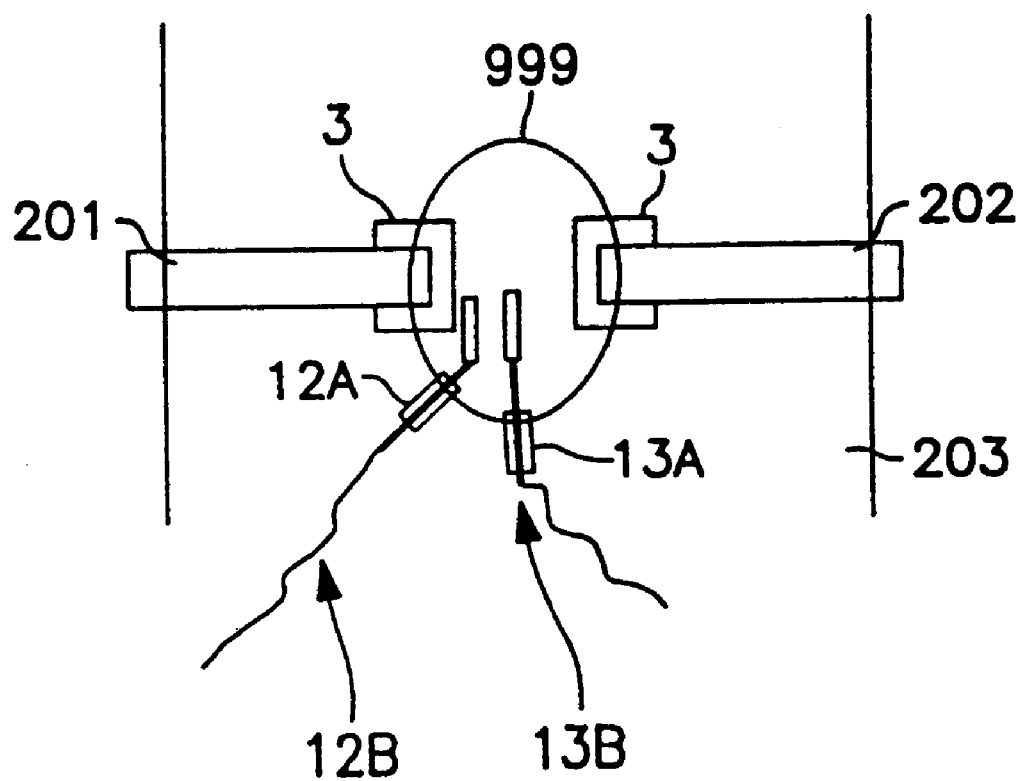
FIG. 20B is a top view of the embodiment shown in FIG.20A.

FIG. 20B is a top view of the embodiment shown in FIG. 20A. As seen, mounted to anchors 201, 202 is a mounting rail 999. In the preferred embodiment mounting rail is ellipsoidal in shape. As seen mounting rail is used to mount slip-grip type holders 12A, 13A and their corresponding suction devices. To be precise, mounting rail permits the suction devices to be securely mounted but yet be easily moved in the area of the surgical procedure. The ellipsoidal shape, moreover, corresponds more suitably to the surgical area. Of course, other shapes may also be used, such as circular, or non-symmetrical, for example. Of course other configurations of a mounting rail, retractor and anchor may be used, such as a retractor integral with the anchors or a mounting rail integral with the retractor or both, to mention only two of the many possibilities.

In use, access to the heart is achieved and retraction of the chest wall is performed prior to the positioning of the anchors. Once the heart access is achieved, the retractor is coupled to the anchors and the anchors are then fixed to the table. At this point, the retractor is thus immobilized with respect to the table and provides a stationary object to which the immobilizing device featuring the a pair of suction devices 12B, 13B may be coupled.

Figure 21:
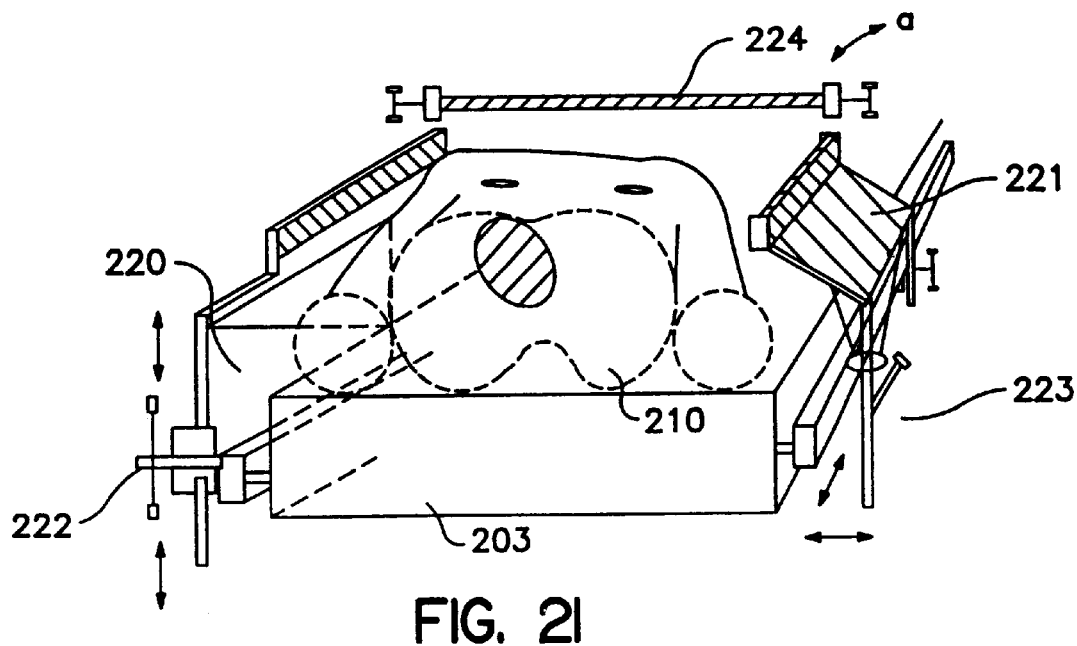
FIG. 21 is a perspective view of a securing device.
Figure 22:
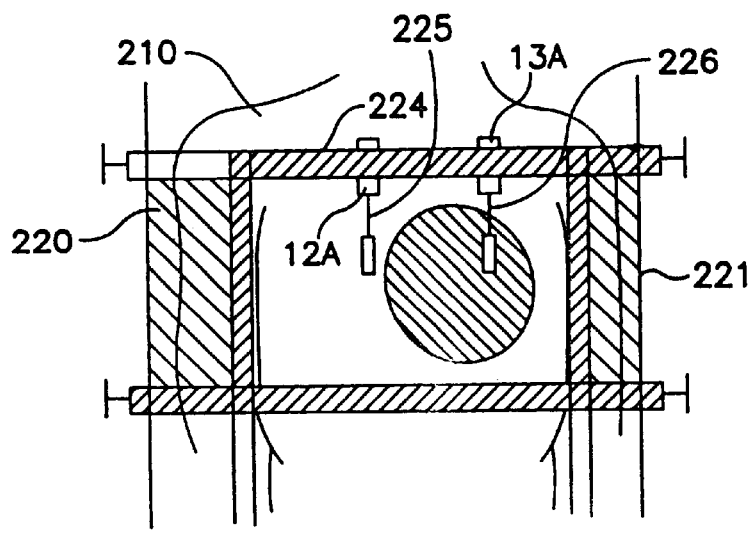
FIG. 22 depicts an overhead view of the securing device.

FIGS. 21 and 22 depict a further alternate embodiment of the securing device. FIG. 21 is a perspective view of a securing device. As seen, in this embodiment, the securing device comprises a pair of formed rails 220, 221. As seen, each rail is coupled to the surgical table 203 through a series of screws 222, 223. Although not shown in the FIGS. each rail further features a truss-like structure such as that shown in FIG. 20A which is positioned below the table which provides additional rigidity and stability. As seen, each rail is further formed to slope inwardly toward the patient 210 (shown in outline in this FIG.) This provides for access above the patient by the surgeon. Straddling between each rail is a mounting 224. The mounting is adjustable along the rail. The mountings are further designed to have a suction device mounted thereto. In such a manner, the mounting 224 and rails 220, 221 provide a stationary object to which the suction device may be mounted.

FIG. 22 depicts an overhead view of the rails 220, 221 used to position a suction device to the heart. As seen, in this embodiment, two suction devices 225, 226 are fastened to the mounting using a pair of slip-grip type holders 12A, 13A as already discussed above.

Figure 23:
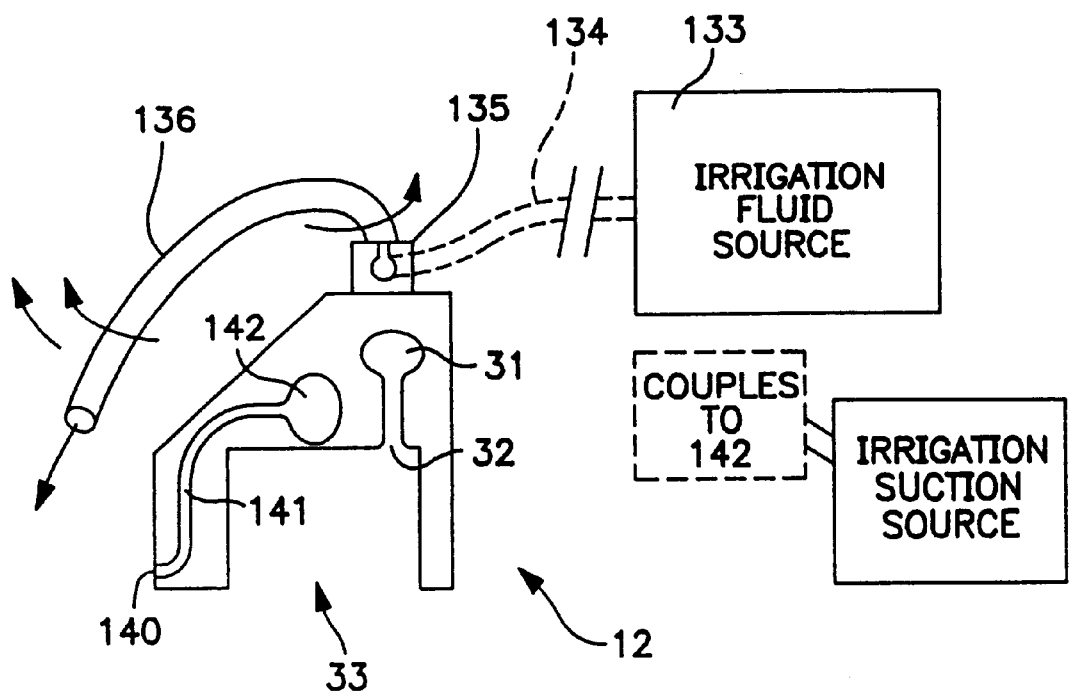
FIG. 23 is a side view of an alternate embodiment of suction device.

Turing now to FIG. 23 which is a side view of an alternate embodiment of suction device 12. As seen this alternate embodiment of suction device 12 features a suction port 33 as already described above. Each suction port is connected to a suction conduit 31 through a suction aperture 32 as also already described above. In this embodiment, however, the suction device further provides for the distribution of irrigation fluid onto the area of the heart where an anastomosis will be performed. As seen, the irrigation fluid source 133 is coupled by an irrigation line 134 to the irrigation fluid conduit 135. The irrigation fluid conduit, in turn, is coupled to an irrigation hose 136. As shown, irrigation hose is designed to have some flexibility to permit it to be rotated and moved along several angles and is preferably a braided stainless steel hose. Irrigation hose dispenses irrigation fluid at its end. Irrigation fluid preferably is a warm saline mist which prevents the exposed tissues from drying out. Moreover, the fluid is dispensed under pressure such that the mist has a force to it which permits the mist to be used to blow with sufficient force to assist in holding open a coronary artery such that the anastomosis may be performed more easily. Suction device further features a return irrigation fluid circuit. As seen, return irrigation fluid circuit comprises a return irrigation port 140 which is coupled to a return irrigation conduit 141. Return irrigation conduit is coupled to a suction source to provide suction to return irrigation pipe 142 such that the irrigation fluid which is dispensed may be readily removed from the surgical area. Although shown as an integral part of the suction device, both the irrigation system as well as the suction system may or may not be a part of the suction device.

Figure 24:
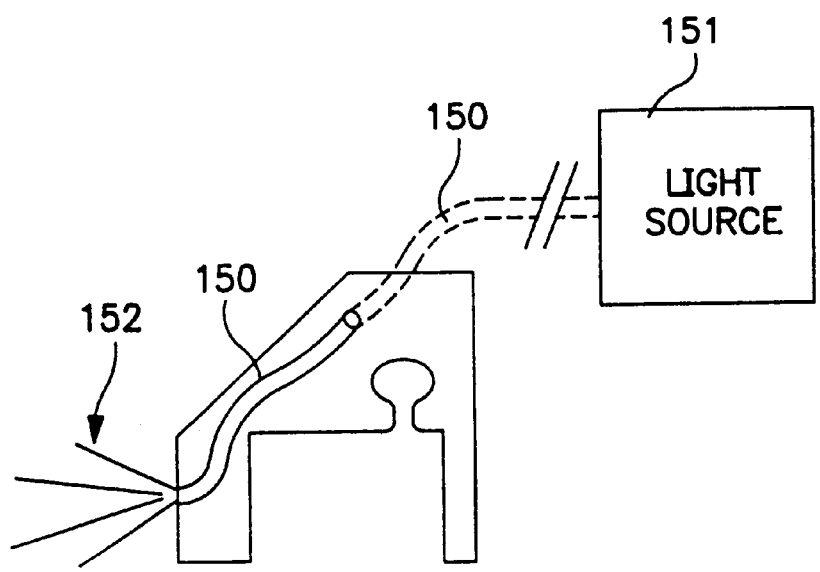
FIG. 24 is a further alternate embodiment of a suction device.

FIG. 24 is a further alternate embodiment of a suction device. As seen, suction device features the suction port, suction conduit and suction aperture as already described above. In this embodiment, however, the suction device further features an optical fiber 150 which is coupled at one end to the area of the suction device where the anastomosis will be performed and is further coupled to a light source 151. In this manner, the suction device may be used to provide additional light 152 to the area where the anastomosis will be performed.

Figure 25:
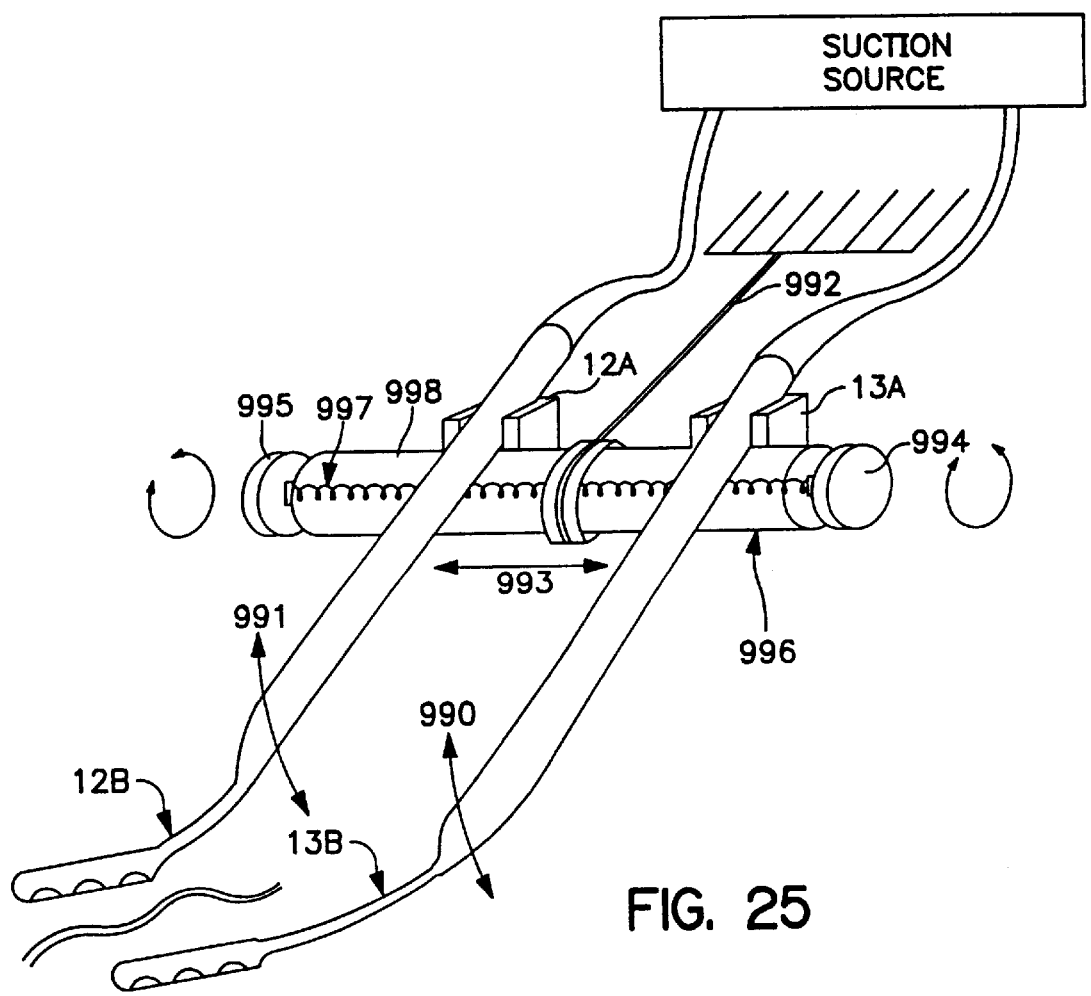
FIG. 25 is a perspective view of an alternate embodiment of an immobilizing device.

FIG. 25 is a perspective view of an alternate embodiment of an immobilizing device 11. As seen, in this embodiment, each suction device is coupled to a mounting beam 998 through a pair of holders 12A, 13A as already described above with reference to FIG. 20A. Mounting beam 998 features two sections, each of which may be individually rotated about or spread apart or both. In particular mounting beam has a central screw members 997, 996. Each central screw member has an actuating knob 994, 995 at an end thereof. Rotation of each knob thereby causes the suction device mounted to that portion of the mounting beam to move either away or towards the center of the mounting beam, as indicated by line 993. Mounting beam 998 is mounted to a stationary object, such as a retractor, mounting rail or fixation arm, through a central arm 992. Each suction device may further be rotated relative to the mounting beam through simply moving each of the relevant devices, as indicated by the lines 991, 990. The use of mounting beam to retain suction devices is of use when only one fixation arm is to be used. In such a manner mounting beam permits both device to be fixed to a stationary object as well as permitting suction devices to be moved apart to thereby provide additional immobilization to a local area of tissue, as discussed above with regards to FIGS. 8–10.

FIG. 26A is a view of the bottom of an alternate embodiment of suction paddle 22 used in the immobilizing device. As seen, paddle has a series of suction ports, each of which is connected to suction conduit through a suction aperture.

In this embodiment, the paddle features five suction ports. The additional side suction port is presented on the side of the suction paddle which will not be near the coronary artery or, in general, the surgical target. The additional port increases the suction surface area. Each suction port 33 has a 6 mm diameter while each suction aperture 32 has a 2 mm diameter.

FIG. 26B is a perspective view of the bottom of an alternate embodiment of suction paddle 22 used in the immobilizing device. As seen in this embodiment the paddle 22 is oriented at a ninety degree angle relative to the neck portion 71 and arm 23. Of course paddle may also be oriented at another suitable angle other than ninety degrees relative to neck portion. In this embodiment, the paddle features four suction ports, although more or less ports may also be provided. Each suction port 33 has a 6 mm diameter while each suction aperture 32 has a 2 mm diameter.

Figure 27:
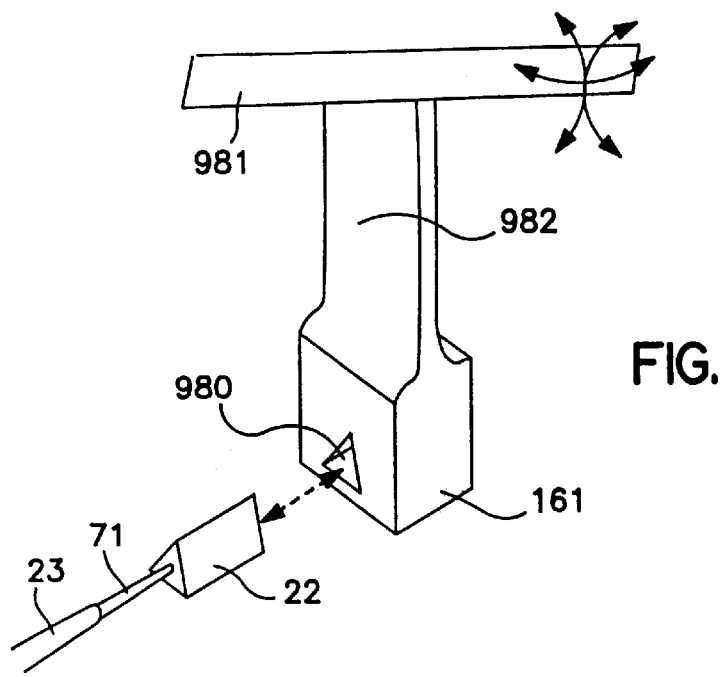
FIG. 27 is a perspective view of a turning handle used to bend or orient the suction paddle portion of the immobilizing device.

FIG. 27 is a perspective view of a turning handle 161 used to bend or orient the suction paddle 22 portion of the immobilizing device. As discussed above neck 71 is fashioned to be relatively bendable, as opposed to paddle 22 and arm 23. As seen, handle 161 features opening 980 having the same shape and dimension of paddle such that paddle may thus be inserted therein. Handle also features neck portion 982 and grip portion 981. Neck and grip portion are dimensioned to provide leverage against opening 980 and thus paddle, neck and arm. To use, paddle is inserted into opening. Once inserted manipulation of grip portion relative to arm causes bending in the area of neck. Such a handle may be advantageous as compared to bending of the device by hand in that it avoids the surgeon from straining hand muscles which will be needed to perform delicate manipulations.

Figure 28:
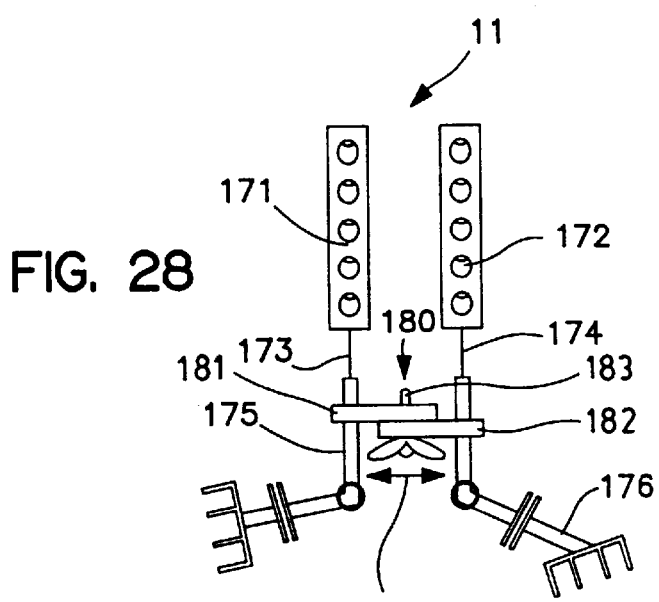
FIG. 28 is a bottom view of an alternate embodiment of immobilizing device.

FIG. 28 is a bottom view of an alternate embodiment of immobilizing device 11. As seen, immobilizing device features a pair of suction paddles 171,172, each of which is coupled to an arm by a continuous hinge or neck as discussed above. The arm in turn, is coupled to a stationary object, also discussed above. In this embodiment, the arms are further fastened together using a spreader 180. As seen, spreader 180 permits the arms to be moved relatively apart or together. As already discussed above, the movement of the arms apart is performed once the paddles are engaging by suction the surface of the heart to thereby increase epicardial tension locally and thus dampen or decrease the motion of the surface of the heart due to the intrinsic beating of the heart. Spreader also functions to provide additional stability to paddles due to its function as a truss-like member.

Figure 29:
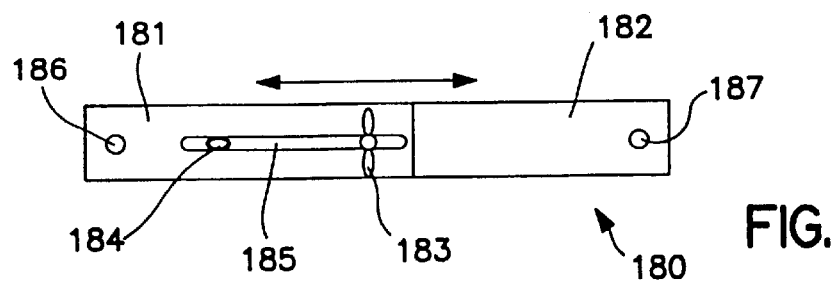
FIG. 29 is a plan view of a spreader used in an alternate embodiment of the present invention.

Turning to FIG. 29, spreader 180 comprises a pair of bars 181, 182 which are coupled together using a wing nut 183. One bar features an engagement pin 184 while the other bar features an engagement slot 185. Each bar is further coupled to each of the respective arms of the immobilizing device by a respective lumen 186, 187. In such a manner, each bar is securely coupled to each arm. By longitudinally manipulating each of the bars apart as shown by arrow 188, each arm and thus each paddle may be securely positioned relatively closer or further apart.

Figure 30:
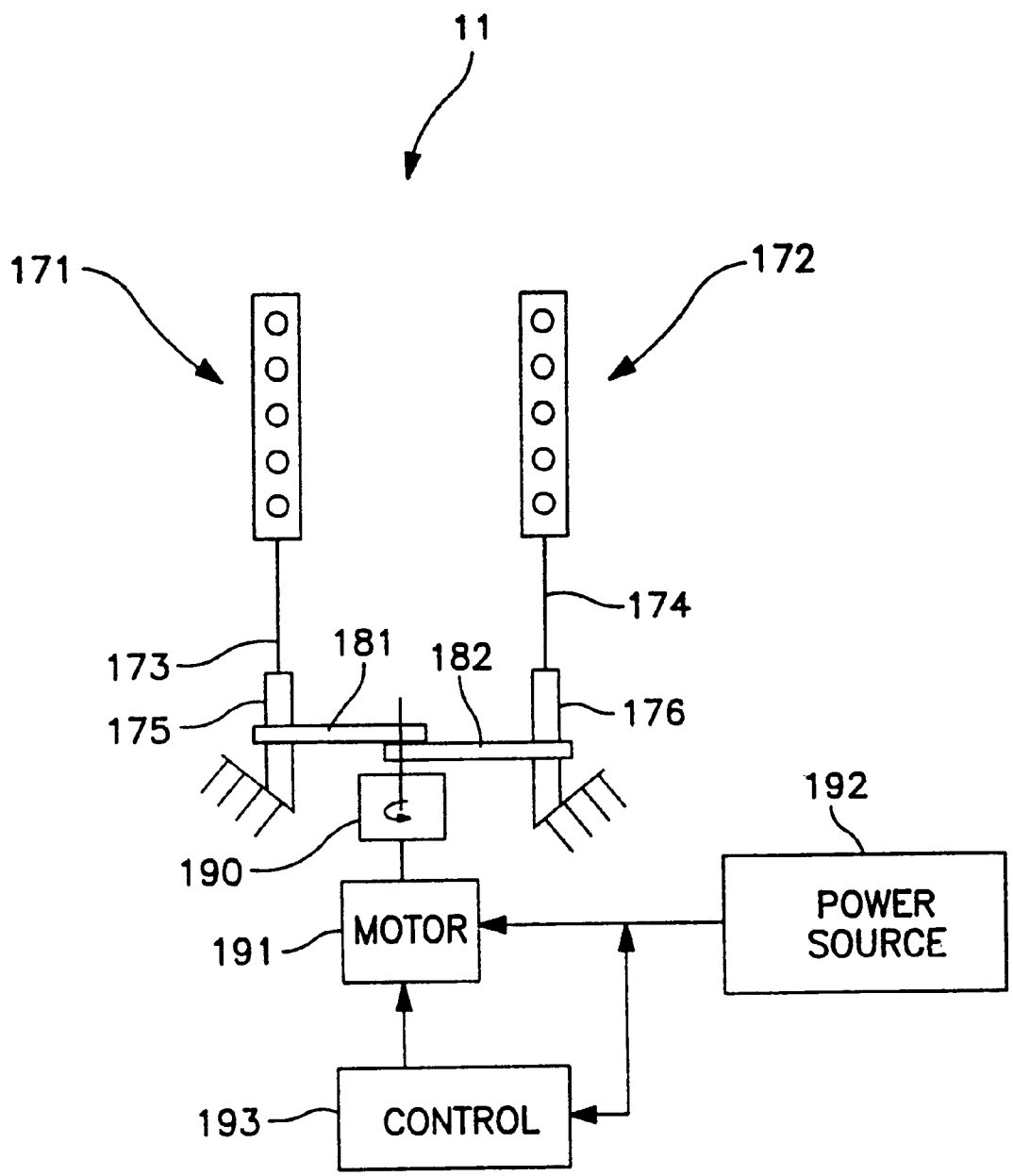
FIG. 30 depicts an alternate embodiment of spreader.

FIG. 30 depicts an alternate embodiment of spreader 180. As seen, spreader features a pair of bars which couple to each of the arms of a respective suction device, as described above. Bars are further coupled together using gearing 190. Gearing, in turn, is coupled to a motor 191. As seen, motor is further coupled to a power source 192. Coupling both motor and power source together is a control 193. Control automatically detects the amount of spread within the suction devices caused by spreader. In the preferred embodiment, control senses the amount of power or energy required by motor to further spread spreader and thus suction paddles apart. When a threshold amount is reached, control shuts down the source of power for motor, thereby locking the spreader in the present position. The feature thus permits a spreader to automatically spread the suction paddles apart to a degree sufficient to dampen wall motion without permitting the spreader to spread paddles apart too much such that capture of the heart wall due to suction is lost. Of course, further designs to control the spreading of suction paddles may also be used, such as other mechanical or hydraulic actuated or controlled systems.

Figure 31:
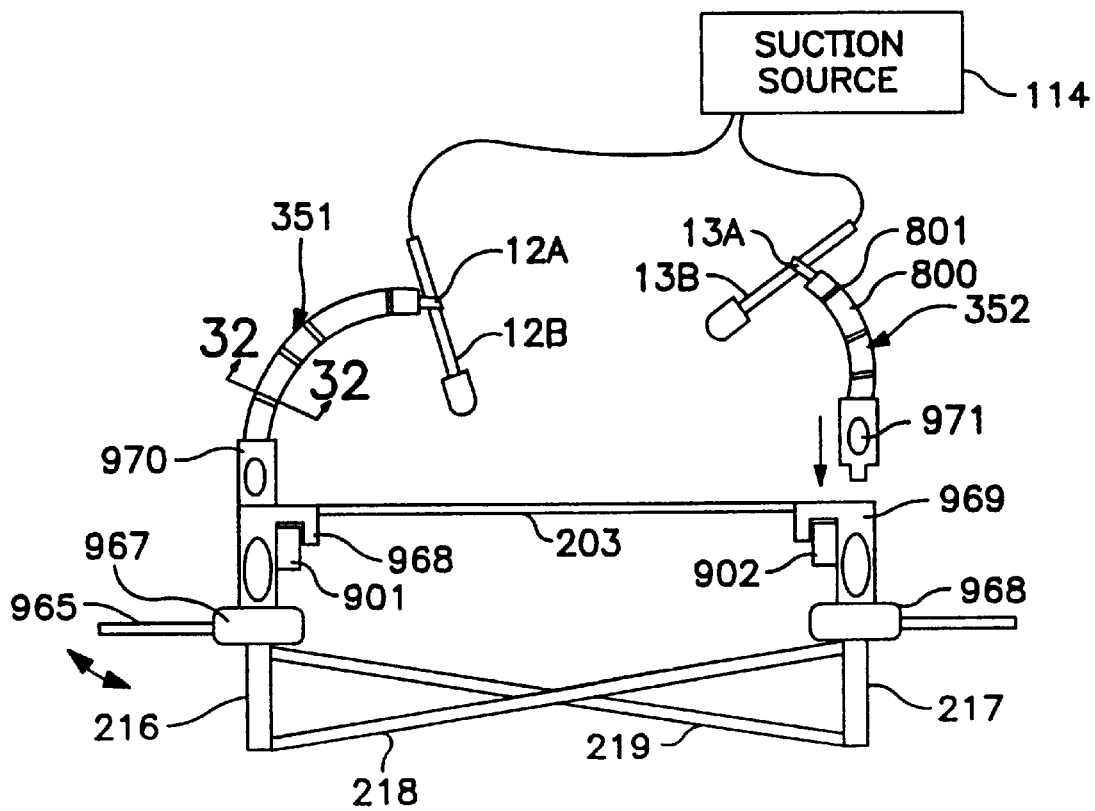
FIG. 31 depicts an alternate embodiment of immobilizing device and, in particular, an alternate embodiment of the securing device used to secure each suction paddle to the operating table rail.

FIG. 31 depicts an alternate embodiment of immobilizing device and, in particular, an alternate embodiment of the securing device used to secure each suction paddle. As seen this system features a pair of arms 351, 351 having a ball and socket construction. As seen each arm features at its free end a slip and grip-type holder 12A and 13A as discussed above. The opposite end of each arm fits into a footing 970, 971. Each footing is lockable to a rail clamp unit 968, 969 which locks onto the rail 901, 902 at the side edges of table 203. Positioned at the bottom of rail clamp unit is locking actuator 967, 968. Each locking actuator cooperates within the arm to thereby cause the arm to be locked into position when the respective handle is turned in one of the directions indicated by arrows 965. In particular locking actuator causes a cable located with the respective arm to tighten, which, due to the ball and socket construction thereby causes the arm to be locked into position. Positioned at the bottom of each locking actuator is a truss. In particular each locking actuator has fixed to it a descending member 216, 217, each of which are linked together by a pair of cross-braces 218, 219. Cross-braces may or may not be coupled together at their center points. As can be appreciated, through this truss construction the stability of anchors and thus the suction devices mounted thereto is increased, as described earlier in FIG. 20A.

Figure 32:
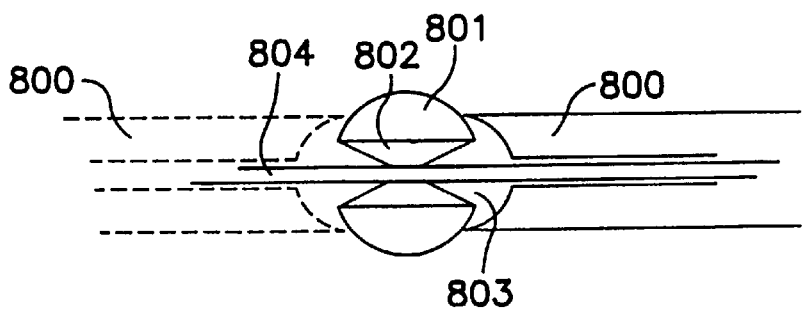
FIG. 32 is a cross sectional view of the arm shown in FIG. 31.

FIG. 32 is a cross sectional view of an arm shown in FIG. 31, and in particular showing a detail of the ball and socket construction. As seen only one portion is shown to illustrate the ball and socket construction. Each tube 800 (several of which are used to create arm) has its end fashioned to correspond to the shape of the ball 801, that is each relevant end of tube features a hemispherical hollow having a radius which corresponds to the outer surface of the ball such that a larger portion of the tube contacts the ball as compared to if the end of the tube were only cut straight across. This geometry increases the surface area between the tube and each ball which thereby increases the stability of the arm when fixed into position. Each ball 801 further features an internal bushing 802. As seen each internal bushing is shaped to have a tapered opening 803 at each end. Positioned through the length of arm, and in particular within each tube element and ball is cable 804. Cable is preferably constructed from kevlar and features a polyurethane covering and is fastened to either end of the arm such that by tensioning the cable the ball and tube portions are brought together and fixed in relation due to friction. The operation of arm is as follows. When no tension is placed on the cable, each tube element may slip relatively easily relative to each ball. Tension on the cable, however, increases the friction between tube and ball. Sufficient tension thereby results in the ball and tube becoming immovable relative to each other. The taper 803 within each bushing 802 permits the cable to remain at the same length regardless of the orientation of each tube element and each ball. That is, if the arm is bent and has a radius of curvature, the taper permits the cable to remain at the same length regardless. This thus permits the arm to be more easily moved and thereafter locked into place.

Figure 33:
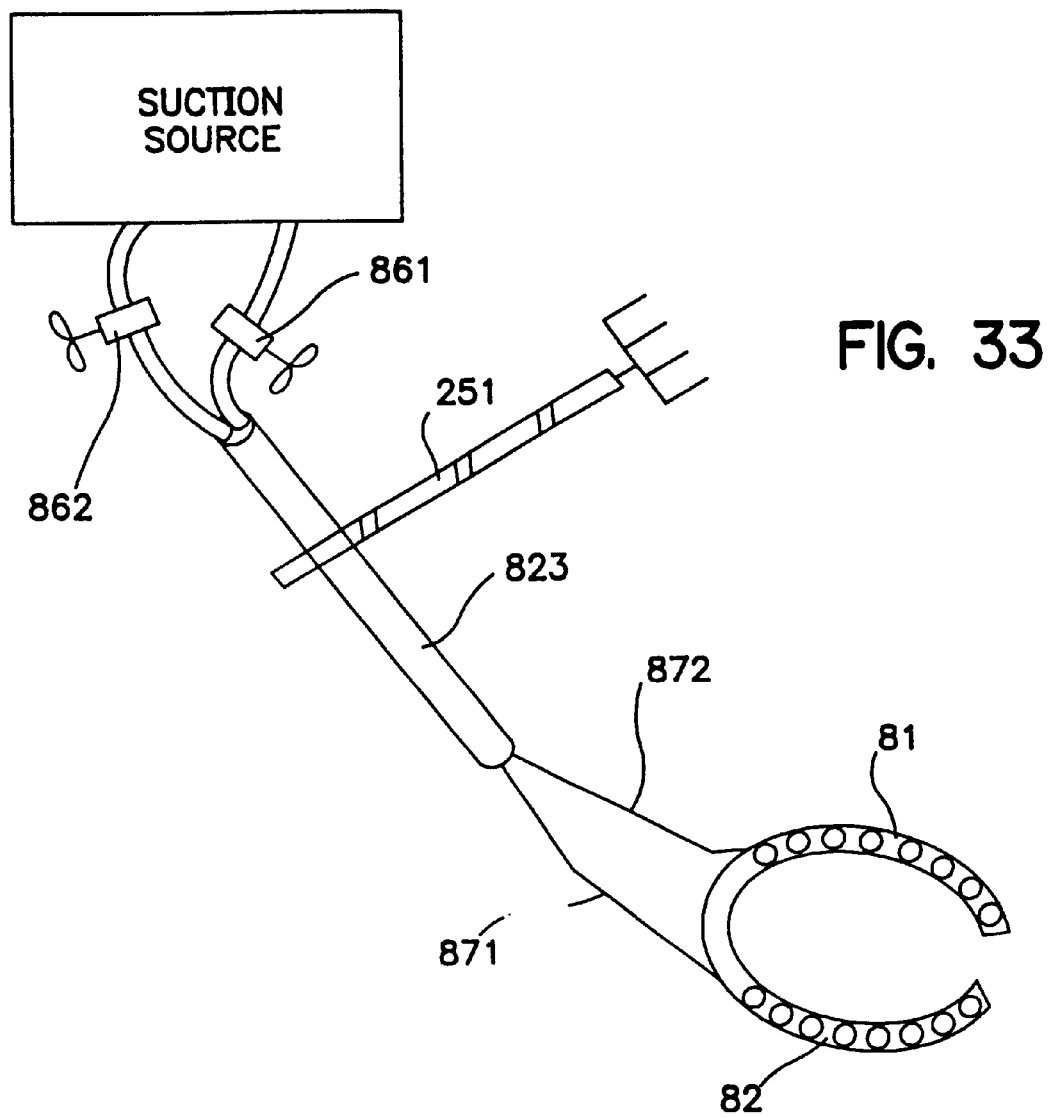
FIG. 33 depicts a further alternate embodiment of the present invention, and in particular of a suction device substantially similar to that shown in FIG. 13 but for that the suction ports are located at the top of the suction paddle.

FIG. 33 depicts a further alternate embodiment of the present invention, and in particular of a suction device substantially similar to that shown in FIG. 13 but for that two separate sets of suction ports are located at the top of the suction paddle. As seen each suction line has a stopcock 861, 862 to permit either or both sets of related suction ports to be independently disconnected from their respective suction source. Arm 823 contains lumens for each suction line and ends where necks 871, 872 begin, As discussed above, each neck is designed to bend. Suction paddle is mounted to necks and as seen features an encircling array of suction ports, located at the upper surface of the paddle relative to the arm. Suction paddle features sixteen suction ports, arranged as a set of eight along one side 81 coupled to one suction line and a second set of eight along another side 82 coupled to another suction line. Through this arrangement even if one side loses capture with the tissue, because the other side is coupled to another suction source, pressure is not lost on that side and capture in that area is maintained. In the embodiment shown the suction ports are located along a generally conical planar surface at the top of the paddle, although other types of planar surfaces may be used, such as frusto-conical for example. The orientation of the suction ports along the top of the encircling paddle is most useful to access the posterior or backside of the heart so as to move or reposition the heart to achieve better access to areas which would otherwise be difficult to access.

To further assist in the exposure of the surgical site, access retractors may also be used in conjunction with the immobilizing device, such as spoon shaped probes to move other tissue from the area of surgical interest.

As disclosed, the present invention relates to a method and apparatus for immobilizing tissue. In the preferred embodiment, the invention is used to immobilize heart tissue for a coronary artery bypass graft procedure using either an open or closed chest approach, without the need for a cardiopulmonary bypass. Other surgical techniques, however, which require immobilizing body tissue may also be performed using the present invention, such as surgery on other organs such as the stomach, gall bladder, etc., as well as on other body tissues, such as the eye or the skin, for example. In addition, while the present invention has been described in detail with particular reference to a preferred embodiment and alternate embodiments, it should be understood variations and modifications can be effected within the scope of the following claims. Such modifications may include substituting elements or components which perform substantially the same function in substantially the same way to achieve substantially the same result for those described herein.

What is claimed is:

1. A method of immobilizing an area of tissue comprising:

contacting a first suction port on a first paddle to a first surface of tissue;

contacting a second suction port on a second paddle to a second surface of tissue;

creating a suction in the first suction port to cause the first suction port to grasp the first surface of the tissue;

creating a suction in the second suction port to cause the second suction port to grasp the second surface of the tissue;

moving the first paddle away from the second paddle;

fixing the first paddle to a stationary object; and fixing the second paddle to a stationary object.

2. A method of immobilizing an area of tissue on a beating heart, the method comprising:

contacting a first suction port on a first paddle to a first surface of tissue on a beating heart;

contacting a second suction port on a second paddle to a second surface of tissue;

creating a suction in the first suction port to cause the first suction port to grasp the first surface of the tissue on the beating heart;

creating a suction in the second suction port to cause the second suction port to grasp the second surface of the tissue on the beating heart;

moving the first paddle away from the second paddle;

fixing the first paddle to a stationary object; and fixing the second paddle to a stationary object.

3. The method of claim 2 further comprising performing surgery on a coronary vessel in an area of the heart between the first and second paddles.

4. The method of claim 3 wherein the step of performing surgery on a coronary vessel in an area of the heart between the first and second paddles includes making an anastomosis to the coronary vessel.

5. The method of claim 4 wherein the steps of fixing the first paddle to a stationary object, and fixing the second paddle to a stationary object each include: fixing the paddle via an arm to a sternal or rib retractor.

6. The method of claim 5 further comprising cutting the patient's sternum and spreading the patient's chest open to expose the heart.

7. The method of claim 6 wherein further comprising orienting and positioning the first and second paddles relative to the heart.

8. The method of claim 7 wherein the step of contacting a first suction port on a first paddle to a first surface of tissue on the beating heart and a second suction port on a second paddle to a second surface of tissue on the beating heart comprises contacting epicardial tissue of the beating heart.

9. The method of claim 8 wherein the step of moving the first paddle away from the second paddle includes turning a handle or knob operationally linked to the first and second paddles to move the first paddle away from the second paddle.

10. A method of immobilizing an area of tissue on a beating heart, the method comprising:

contacting a first suction port on a first paddle to a first surface of tissue on the beating heart and a second suction port on a second paddle to a second surface of tissue on the beating heart;

creating a suction in the first and second suction ports to cause the first and second suction ports to grasp the first and second surfaces of tissue on the beating heart;

moving the first paddle away from the second paddle;

fixing the first and second paddles to a stationary object.

11. The method of claim 10 further comprising performing surgery on a coronary vessel in an area of the heart between the first and second paddles.

12. The method of claim 11 wherein the step of performing surgery on a coronary vessel in an area of the heart between the first and second paddles includes making an anastomosis to the coronary vessel.

13. The method of claim 12 wherein the step of fixing the first and second paddles to a stationary object include:

fixing the first and second paddles via at least one arm to a sternal or rib retractor.

14. The method of claim 13 further comprising cutting the patient's sternum and spreading the patient's chest open to expose the heart.

15. The method of claim 14 further comprising orienting and positioning the first and second paddles relative to the heart.

16. The method of claim 15 wherein the step of orienting and positioning the first and second paddles relative to the heart includes bending the at least one arm.

17. The method of claim 16 wherein the step of contacting a first suction port on a first paddle to a first surface of tissue on the beating heart and a second suction port on a second paddle to a second surface of tissue on the beating heart comprises contacting epicardial tissue of the beating heart.

18. The method of claim 17 wherein the step of moving the first paddle away from the second paddle includes turning a handle or knob operationally linked to the first and second paddles to move the first paddle away from the second paddle.

19. The method of claim 13 further comprising orienting and positioning the first and second paddles relative to the heart.

20. The method of claim 19 wherein the step of orienting and positioning the first and second paddles relative to the heart includes bending the at least one arm.

21. The method of claim 10 further comprising orienting and positioning the first and second paddles relative to the heart.

22. The method of claim 10 wherein the step of fixing the first and second paddles to a stationary object comprises mounting a single arm to a stationary object to fix the first and second paddles.

23. A method of immobilizing an area of tissue on a beating heart to thereby permit surgery on a coronary vessel in that area without significant deterioration of the pumping function of the beating heart, the method comprising:

cutting the patient's sternum and opening the patient's thoracic cavity with a sternal retractor to expose the heart;

contacting a first suction port on a first paddle to a first surface of epicardial tissue on the beating heart and a second suction port on a second paddle to a second surface of epicardial tissue on the beating heart;

creating a suction in the first and second suction ports to cause the first and second suction ports to grasp the first and second surfaces of epicardial tissue on the beating heart;

moving the first paddle away from the second paddle;

fixing the first and second paddles to the sternal retractor; and performing surgery on a coronary vessel in an area of the heart between the first and second paddles.

24. The method of claim 23 wherein the step of performing surgery on a coronary vessel in an area of the heart between the first and second paddles includes making an anastomosis to the coronary vessel.

25. The method of claim 23 wherein the step of moving the first paddle away from the second paddle includes turning a handle or knob operationally linked to the first and second paddles to move the first paddle away from the second paddle.

26. A method of immobilizing an area of tissue on a beating heart to thereby permit surgery on a coronary vessel in that area without significant deterioration of the pumping function of the beating heart, the method comprising:

cutting the patient's sternum and opening the patient's thoracic cavity with a sternal retractor to expose the heart;

contacting a first tissue-engaging surface on a first paddle to epicardial tissue on the beating heart and a second tissue-engaging surface on a second paddle to epicardial tissue on the beating heart;

creating suction along the first and second tissue-engaging surfaces to cause the first and second paddles to grasp epicardial tissue on the beating heart to define a relatively immobilized area along the epicardial surface between the first and second paddles;

fixing the first and second paddles to the sternal retractor; and performing surgery on a coronary vessel in the relatively immobilized area.

27. The method according to claim 26 wherein the first and second tissue-engaging surfaces conform generally to the curvature of a heart.

28. The method according to claim 26 further comprising orienting the paddle along any of three normal axes.

29. The method according to claim 28 wherein the step of fixing the first and second paddles to the sternal retractor includes fixing at least one paddle to the sternal retractor via an arm, and the step of orienting the paddle along any of three normal axes comprises bending the arm.

30. The method according to claim 29 wherein the arm has a plurality of joints or hinges, and the step of bending the arm comprises moving the joints or hinges and locking the joints or hinges.

31. A method of grasping epicardial tissue on a beating heart without significant deterioration of the pumping function of the beating heart, the method comprising:

contacting first and second tissue-engaging means to epicardial tissue on the beating heart;

creating suction along the first and second tissue-engaging means to cause the first and second tissue-engaging means to grasp epicardial tissue on the beating heart;

mounting the first and second tissue-engaging means via an arm to the sternal retractor without significant deterioration of the pumping function of the beating heart; and performing surgery on a coronary vessel.

32. A method of grasping epicardial tissue on a beating heart without significant deterioration of the pumping function of the beating heart, the method comprising:

cutting through the sternum of a patient;

mounting a sternal retractor on the sternum and spreading the chest of the patient open with the sternal retractor to expose the heart;

contacting first and second tissue-engaging members to epicardial tissue on the beating heart;

creating suction along the first and second tissue-engaging members to cause the first and second tissue-engaging means to grasp epicardial tissue on the beating heart;

fixing the first and second tissue-engaging members relative to the sternal retractor without significant deterioration of the pumping function of the beating heart; and performing surgery on a coronary vessel.

33. The method of claim 32 further comprising orienting and positioning the first and second tissue-engaging members relative to the heart.

34. The method of claim 33 wherein the step of fixing the first and second tissue-engaging members relative to the sternal retractor without significant deterioration of the pumping function of the beating heart includes:

fixing the first and second tissue-engaging members via at least one arm to the sternal retractor.

35. The method of claim 34 wherein the step of orienting and positioning the first and second tissue-engaging members relative to the heart includes bending the at least one arm.

36. The method according to claim 34 wherein the step of creating suction along the first and second tissue-engaging members to cause the first and second tissue-engaging means to grasp epicardial tissue on the beating heart includes:

creating about 200–600 mm Hg of suction.

37. A method of grasping epicardial tissue on a beating heart without significant deterioration of the pumping function of the beating heart, the method comprising:

contacting first and second tissue-engaging members to epicardial tissue on the beating heart;

creating suction along the first and second tissue-engaging members to cause the first and second tissue-engaging members to grasp epicardial tissue on the beating heart;

fixing the first and second tissue-engaging members to a stationary object without significant deterioration of the pumping function of the beating heart; and performing a coronary artery bypass graft without requiring the heart to be arrested or stopped and the patient coupled to a cardiopulmonary bypass machine.

38. The method according to claim 37 wherein the first and second tissue-engaging members each have tissue contacting surfaces conforming generally to the curvature of a heart.

39. The method according to claim 37 further comprising orienting at least one of the first and second tissue-engaging members along any of three normal axes.

40. The method according to claim 39 wherein the step of fixing the first and second tissue-engaging members to a stationary object without significant deterioration of the pumping function of the beating heart includes fixing at least one of the first and second tissue-engaging members to the stationary object via an arm, and the step of orienting at least one of the first and second tissue-engaging members along any of three normal axes comprises bending the arm.

41. The method according to claim 40 wherein the arm has a plurality of joints or hinges, and the step of bending the arm comprises moving the joints or hinges and locking the joints or hinges.

42. The method according to claim 41 further comprising accessing the heart through minimally invasive means, the step of moving the joints or hinges and locking the joints or hinges comprising remotely actuating the joints or hinges.

43. The method according to claim 42 wherein the minimally invasive means are selected from the group consisting of small stab wound or incision, mini-thoracotomy and trocar.

44. The method according to claim 43 wherein the stationary object is a portion of the patient's skeletal system.

45. The method according to claim 37 wherein the step of creating suction along the first and second tissue-engaging members to cause the first and second tissue-engaging members to grasp epicardial tissue on the beating heart comprises creating about 200–600 mm Hg of suction.

46. A method of immobilizing an area of tissue on a beating heart without significant deterioration of the pumping function of the beating heart, the method comprising:

contacting first and second tissue-engaging members to epicardial tissue on the beating heart, thereby defining an area of tissue between the first and second tissue-engaging members;

creating suction along the first and second tissue-engaging members to cause the first and second tissue-engaging members to grasp epicardial tissue on the beating heart;

mounting the first and second tissue-engaging members to a stationary object to substantially immobilize the area of tissue between the first and second tissue-engaging members without significant deterioration of the pumping function of the beating heart; and performing a coronary artery bypass graft without requiring the heart to be arrested or stopped and the patient coupled to a cardiopulmonary bypass machine.

47. The method of claim 46 wherein the step of contacting first and second tissue-engaging members to epicardial tissue on the beating heart includes positioning the first and second tissue-engaging members on epicardial tissue on opposite sides of a coronary artery upon which a graft is to be made.

48. The method according to claim 47 wherein the stationary object is a portion of the patient's skeletal system.

49. The method according to claim 46 wherein the step of creating suction along the first and second tissue-engaging members to cause the first and second tissue-engaging members to grasp epicardial tissue on the beating heart comprises creating about 200–600 mm Hg of suction.

50. The method according to claim 46 further comprising orienting at least one of the first and second tissue-engaging members along any of three normal axes.

51. The method according to claim 46 further comprising creating a high resistance pathway that permits the loss of seal to epicardial tissue along a portion of the first or second tissue-engaging members without causing a precipitous pressure drop in the remainder of the first or second tissue-engaging means.

52. The method according to claim 51 wherein the first and second tissue engaging members include a plurality of suction ports and at least one suction aperture within each suction port communicating suction to epicardial tissue, the suction aperture having a smaller cross section than the suction port.

53. The method according to claim 52 wherein the suction apertures are positioned within the suction port to avoid blockage of suction to the epicardial tissue.

54. The method according to claim 46 further comprising releasing suction and removing the first and second tissue-engaging members from the heart.

55. The method according to claim 54 wherein the step of performing a coronary artery bypass graft without requiring the heart to be arrested or stopped and the patient coupled to a cardiopulmonary bypass machine includes grafting a mammary artery to a coronary artery.

56. The method according to claim 55 wherein the step of grafting a mammary artery to a coronary artery comprises grafting a mammary artery end-to-side to a coronary artery.

57. The method according to claim 46 further comprising mobilizing an artery or vein.

58. The method according to claim 57 wherein the step of mobilizing an artery or vein comprises mobilizing a mammary artery or a saphenous vein.

59. A method of immobilizing an area of tissue on a beating heart without significant deterioration of the pumping function of the beating heart, the method comprising:

contacting at least one primary suction port on a first paddle to a first area of tissue of the beating heart;

contacting at least one secondary suction port on a second paddle to a second area of tissue of the beating heart;

creating a suction in at least one primary suction port to cause the first paddle to grasp the first area of tissue of the beating heart;

creating a suction in at least one secondary suction port to cause the second paddle to grasp the second area of tissue of the beating heart;

moving the first paddle away from the second paddle to tension a third area of tissue of the beating heart between the first and second areas of tissue; and fixing at least one of the first and second paddles to a stationary object, to thereby immobilize the third area of tissue of the beating heart without significant deterioration of the pumping function of the beating heart.

60. The method of claim 59 wherein the steps of contacting at least one primary suction port on a first paddle to a first area of tissue of a beating heart, and contacting at least one secondary suction port on a second paddle to a second area of tissue of a beating heart includes:

positioning the first and second paddles on epicardial tissue on opposite sides of a coronary artery upon which a graft is to be made.

61. The method according to claim 60 wherein the stationary object is a portion of the patient's skeletal system.

62. The method according to claim 59 wherein the steps of creating a suction in at least one primary suction port to cause the first paddle to grasp the first area of tissue of the beating heart; and creating a suction in at least one secondary suction port to cause the second paddle to grasp the second area of tissue the beating heart each include:

creating about 200–600 mm Hg of suction.

63. The method according to claim 59 further comprising orienting at least one of the first and second paddles along any of three normal axes.

64. The method according to claim 59 further comprising releasing suction and removing the first and second paddles from the heart.

* * * * *